US009488602B2

(12) United States Patent
Kobayashi et al.

(10) Patent No.: US 9,488,602 B2
(45) Date of Patent: Nov. 8, 2016

(54) RADIOACTIVE SUBSTANCE DETECTION DEVICE, RADIATION SOURCE LOCATION VISIBILITY SYSTEM, AND RADIOACTIVE SUBSTANCE DETECTION METHOD

(71) Applicant: National Institute of Radiological Sciences, Chiba-shi, Chiba (JP)

(72) Inventors: Shingo Kobayashi, Chiba (JP); Yukio Uchihori, Chiba (JP); Yoshiyuki Shirakawa, Chiba (JP)

(73) Assignee: National Institutes for Quantum and Radiological Science and Technology, Chiba-shi, Chiba (JP)

( * ) Notice: Subject to any disclaimer, the term of this patent is extended or adjusted under 35 U.S.C. 154(b) by 144 days.

(21) Appl. No.: 14/346,856

(22) PCT Filed: Jan. 12, 2013

(86) PCT No.: PCT/JP2013/000114
§ 371 (c)(1),
(2) Date: Mar. 24, 2014

(87) PCT Pub. No.: WO2013/105519
PCT Pub. Date: Jul. 18, 2013

(65) Prior Publication Data
US 2014/0299784 A1 Oct. 9, 2014

(30) Foreign Application Priority Data

Jan. 13, 2012 (JP) ................................. 2012-005699

(51) Int. Cl.
*G01N 23/00* (2006.01)
*G01T 7/00* (2006.01)
*G01T 1/164* (2006.01)

(52) U.S. Cl.
CPC ............. *G01N 23/00* (2013.01); *G01T 1/1648* (2013.01); *G01T 7/00* (2013.01)

(58) Field of Classification Search
CPC ........ G01N 23/00; G01T 1/1648; G01T 7/00
USPC .................................. 250/394, 336.1, 378.1
See application file for complete search history.

(56) References Cited

U.S. PATENT DOCUMENTS 2,736,815 A * 2/1956 Marshall ............... G01T 1/2004
250/485.1
3,581,090 A * 5/1971 Brown .................. G01T 1/2907
250/363.01

(Continued)

FOREIGN PATENT DOCUMENTS

| JP | 7-209493 | 8/1995 |
| JP | 11-64529 | 3/1999 |

(Continued)

*Primary Examiner* — Marcus Taningco
*Assistant Examiner* — Gisselle Gutierrez
(74) *Attorney, Agent, or Firm* — Hamre, Schumann, Mueller & Larson, P.C.

(57) ABSTRACT

A radioactive substance detection device that detects a radioactive substance being present in a specified direction. A radiation detection element having a thickness that stops and detects a characteristic X-ray arriving from a radioactive substance being present in the specified direction that radiates both gamma rays and the characteristic X-rays, and allows the gamma ray arriving from the radioactive substance to pass through. A screening body having a thickness that screens out characteristic X-rays of radiation which arrives from directions other than the specified direction and allows gamma rays of radiation which arrives from directions other than the specified direction to pass through.

13 Claims, 12 Drawing Sheets

(56) References Cited

U.S. PATENT DOCUMENTS

| | | | | |
|---|---|---|---|---|
| 4,033,885 A * | 7/1977 | Stone | ............ | G21K 1/025 250/496.1 |
| 5,519,227 A * | 5/1996 | Karellas | ............ | G21K 4/00 250/370.11 |
| 5,659,177 A * | 8/1997 | Schulte | ............ | G01T 3/08 250/370.05 |
| 7,026,627 B2 * | 4/2006 | Fowler, Jr. | ............ | G01T 1/169 250/390.12 |
| 7,470,909 B2 * | 12/2008 | Larsson | ............ | G01T 1/169 250/370.09 |
| 8,237,129 B2 * | 8/2012 | Sullivan | ............ | G01T 3/08 250/390.01 |
| 8,592,775 B2 * | 11/2013 | Workman | ............ | G01T 3/06 250/390.01 |
| 2004/0054248 A1 * | 3/2004 | Kimchy | ............ | A61B 5/055 600/3 |
| 2004/0156478 A1 * | 8/2004 | Appleby | ............ | B23P 15/246 378/147 |
| 2005/0105665 A1 * | 5/2005 | Grodzins | ............ | G01T 3/06 376/157 |
| 2005/0121618 A1 * | 6/2005 | Fowler | ............ | G01T 1/169 250/394 |
| 2007/0221854 A1 * | 9/2007 | Shirakawa | ............ | G01T 1/169 250/367 |
| 2008/0048123 A1 * | 2/2008 | Larsson | ............ | G01T 1/2907 250/363.01 |
| 2008/0149838 A1 * | 6/2008 | Parvin | ............ | G01S 7/4802 250/356.2 |
| 2009/0175412 A1 * | 7/2009 | Grodzins | ............ | G01N 23/04 378/57 |
| 2011/0170778 A1 | 7/2011 | Le Goaller et al. | | |
| 2012/0049073 A1 * | 3/2012 | Den | ............ | G01T 1/1642 250/361 R |
| 2013/0099125 A1 * | 4/2013 | Grodzins | ............ | G01T 1/2008 250/362 |
| 2014/0291531 A1 * | 10/2014 | Dai | ............ | G01T 1/167 250/366 |

FOREIGN PATENT DOCUMENTS

| | | |
|---|---|---|
| JP | 2001-208856 | 8/2001 |
| JP | 2004-85250 | 3/2004 |
| JP | 2008-96401 | 4/2008 |
| JP | 2010-101663 | 5/2010 |
| JP | 2011-524532 | 9/2011 |

* cited by examiner

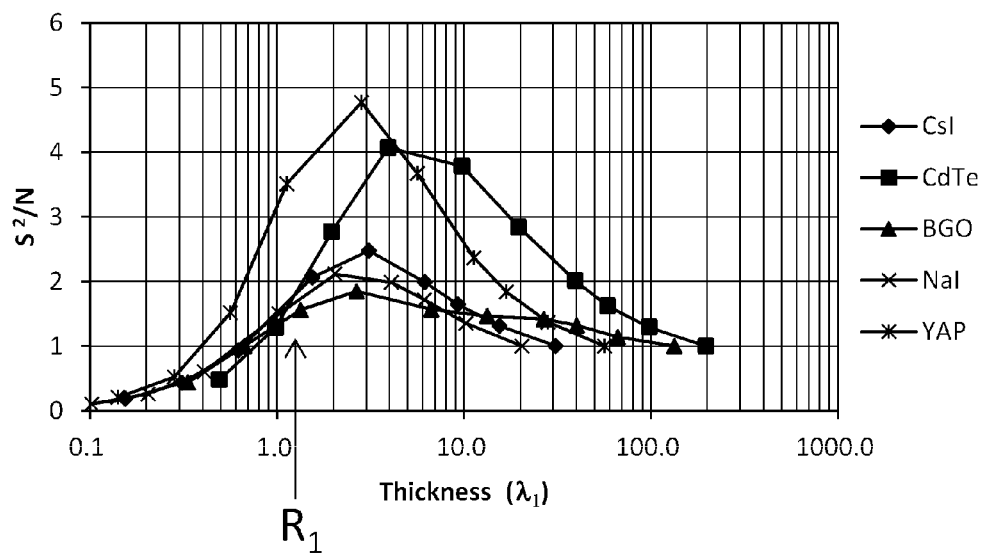
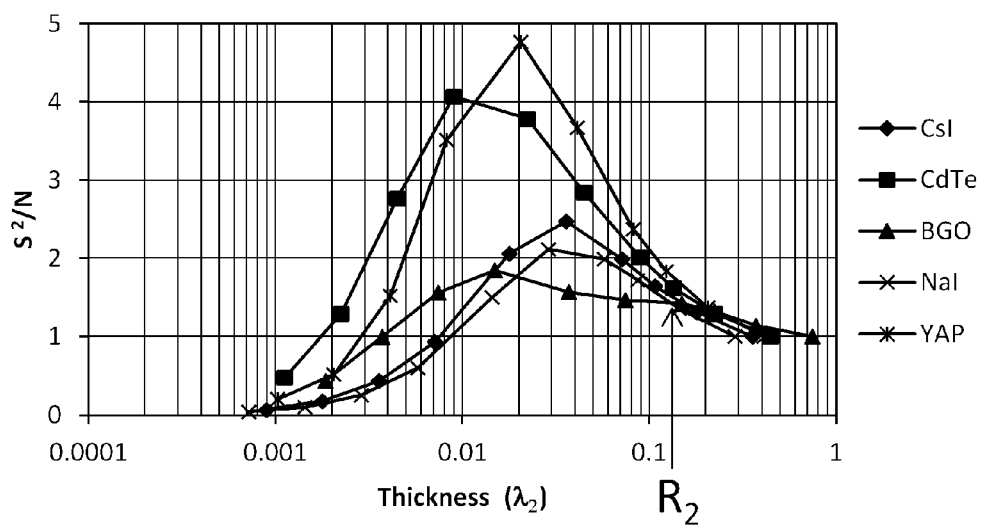

RADIOACTIVE SUBSTANCE DETECTION DEVICE, RADIATION SOURCE LOCATION VISIBILITY SYSTEM, AND RADIOACTIVE SUBSTANCE DETECTION METHOD

TECHNICAL FIELD

The present invention relates to a radioactive substance detection device, a radiation source location visualization system, and a radioactive substance detection method with which a radioactive substance which radiates, for example, both gamma rays and characteristic X-rays is detected.

BACKGROUND ART

Conventionally, a gamma camera is used for identifying the position where a radioactive substance is present in environments where radiation arrives from a variety of directions, for example, in a nuclear power plant, a nuclear fuel or spent nuclear fuel processing facility, or in nuclear emergency situations. As such a gamma camera, a radiation measurement device is proposed (see Patent Document 1).
[Patent Document 1] Japanese Patent Application Laid-Open No. 2004-85250

This radiation measurement device includes a multiple collimator having a plurality of holes that allow components of predetermined directions of gamma rays radiated from a radioactive substance to pass through, a fluorescent screen that converts gamma rays having passed through the multiple collimator to visible light, and a screening container that covers the multiple collimator and the fluorescent screen to reduce radiation noise. The radiation measurement device combines a gamma ray image and an image photographed by another camera. In this manner, the radiation measurement device can grasp the condition, size, shape, and position of the internal radioactive substance as a radiation image for an object to be measured.

However, such a radiation measurement device is disadvantageously very heavy because it detects gamma rays radiated from the radioactive substance. To be more specific, in an environment where radiation arrives from a variety of directions, the screening container needs to screen out gamma rays arriving from other directions for grasping the direction from which the gamma rays arrive. For screening out gamma rays, the screening container needs to use thick lead. Also, for detecting gamma rays, the fluorescent screen is required to have sufficient thickness and high density to prevent gamma rays from passing through.

For example, in the case of detecting gamma rays having an energy of 662 keV radiated from $^{137}$Cs and grasping the arriving direction thereof, a fluorescent screen 126 provided in the previous stage of a photomultiplier 27, and a screening container 125 covering these are as shown in FIG. 12. That is, in the case of screening out gamma rays at an efficiency of 98%, the screening container 125 has a thickness of about 34 mm when lead having a specific gravity of 11.3 is used. When NaI (diameter 50 mm) having a specific gravity of 3.7 is used as the substance, the fluorescent screen 126 will have a thickness of about 10 mm for detecting gamma rays at an efficiency of 8%. So assuming that the radiation measurement device 102 is fabricated to have such a format that the field of view is ±22 degrees by a single collimator 121 having only one hole that allows a predetermined direction component to pass through, and light emission of the fluorescent screen by gamma rays is read by a photomultiplier of 65 mm long, the weight is about 25 kg only by the screening container 125 and the fluorescent screen 126, which is heavy to carry.

If lead that forms the screening container were to be thinned or if the fluorescent screen were to be thinned, the radiation measurement device would be light in weight. However, in such a radiation measurement device whose weight is reduced in this manner, disadvantageously, the accuracy is significantly impaired. That is, if the thickness of lead of the screening container is thinned, the radiation measurement device will detect gamma rays arriving from directions other than the predetermined direction, whereas if the fluorescent screen is thinned, the sensitivity will be impaired due to increased transmission amount of gamma rays. Therefore, in detecting a radioactive substance radiating gamma rays, thinning the screening container is limited, and also thinning the fluorescent screen is limited due to the relation with sensitivity.

SUMMARY OF THE INVENTION

In light of the aforementioned problems, it is an object of the present invention to provide a radioactive substance detection device, a radiation source location visualization system, and a radioactive substance detection method, which are usable in an environment where radiation arrives from various directions, and which have substantially lower weight and with which sufficient performance is obtained.

The present invention provides a radioactive substance detection device for detecting a radioactive substance being present in a specified direction in an environment where radiation arrives from various directions, and the radioactive substance detection device includes a radiation detection element having a thickness which stops and detects characteristic X-rays arriving from the radioactive substance being present in the specified direction and radiating both gamma rays and the characteristic X-rays, and which allows the gamma rays arriving from the radioactive substance to pass through, and a screening body having a thickness which screens out characteristic X-rays of radiation which arrives from directions other than the specified direction, and allows gamma rays of the radiation which arrives from the directions other than the specified direction to pass through.

According to the present invention, it is thus possible to provide a radioactive substance detection device, a radiation source location visualization system, and a radioactive substance detection method, which are usable in an environment where radiation arrives from various directions, and have substantially lower weight and with which sufficient performance is obtained.

BRIEF DESCRIPTION OF THE DRAWINGS

FIGS. 1A and 1B are explanatory charts by graphs showing thickness and performance of a radiation detection element.

EMBODIMENTS OF THE INVENTION

Figure 2A:
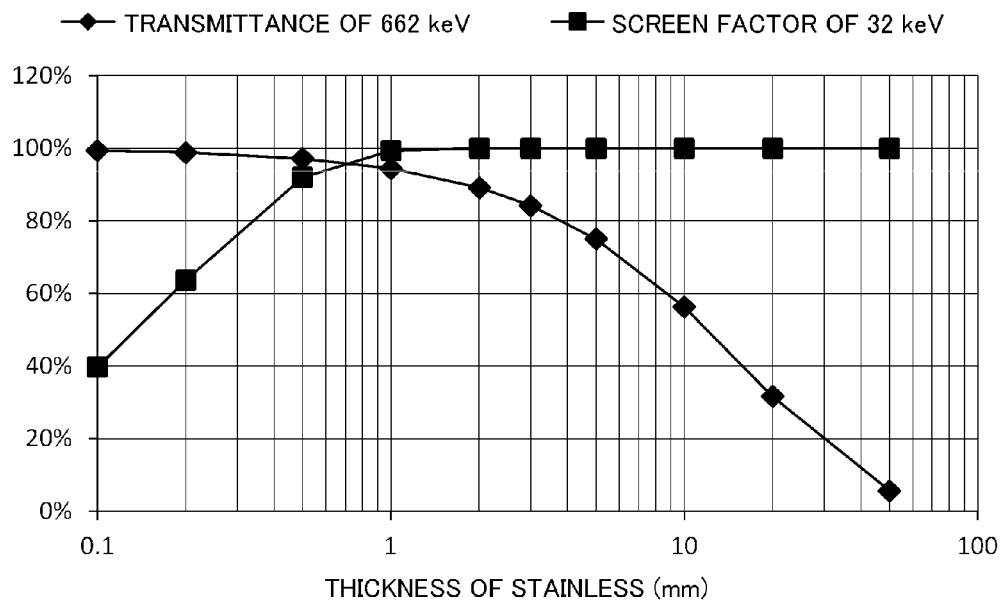
FIGS. 2A and 2B are explanatory charts for explaining changes in screening, transmission and background with the change in thickness of a screening container.

In detection of a radioactive substance, it is generally preferred to detect gamma rays radiated from the radioactive substance. This is because since gamma rays have high energy, it is easy to measure from the point of signal-to-noise ratio in a signal processing circuit of a radiation measurement device, and background is lower in a gamma ray region of high energy generally in an environment where gamma rays are radiated, and a large number of gamma rays are radiated per one decay of the radioactive substance. However, when the screening container is thinned for reducing the weight of the gamma camera, the directional sensitivity is impaired because of transmission of gamma rays, and when the radiation detection element is thinned, the detection sensitivity of gamma rays is impaired.

The present inventors made diligent efforts for reducing the weight of a gamma camera that detects a radioactive substance. First, the inventors attempted to reduce the weight of the gamma camera by using a material of light weight and small size having high detection sensitivity for gamma rays as a gamma ray detection element to make the gamma ray detection element compact, and by reducing the weight of lead for a screening container and a collimator constituting a screening body. However, in this approach, it is impossible to significantly reduce the weight, for example, to make the screening body one-eighteenth or less of the conventional one.

Then, the present inventors mainly focused on, in addition to gamma rays radiated from the radioactive substance, the gamma rays that is generated by scattering of the gamma rays by a normal substance being present near the radioactive substance (energy region of mainly around 200 keV). Accordingly, the inventors considered about making the gamma ray detection element compact by increasing the count rate of gamma rays by measuring gamma rays including these scattered gamma rays of this energy region. As a result, further increase in sensitivity of the gamma camera is expected, and weight of lead for the screening container and the collimator constituting the screening body can be reduced. However, actually, intensity of the scattered gamma rays changes depending on the arrangement of a substance being present around the radioactive substance, and in this measure, there is a problem that quantity of the radioactive substance cannot be measured satisfactorily. In addition, it is also impossible with this measure to significantly reduce the weight of the screening body, for example, to one-eighteenth or less of the conventional one.

The present inventors further made diligent efforts, and focused on characteristic X-rays generated from a radioactive substance. Then, the present inventors attempted to detect presence of a radioactive substance by detecting the characteristic X-rays. In general, characteristic X-rays, which are low in radiation probability and low in energy in comparison with gamma rays, are difficult to be measured, and thus have not been noted heretofore. The present inventors made the signal processing circuit of the radioactive substance detection device be able to measure characteristic X-rays of a low energy region for detecting characteristic X-rays, and attempted to further reduce noises. However, there is a problem that characteristic X-rays cannot be satisfactorily detected due to high background generated by gamma rays scattering with the radioactive substance detection device.

In light of the above, the present inventors made further diligent efforts, and succeeded in detecting presence of a radioactive substance with a device of light weight by employing such a configuration of excluding gamma rays as much as possible, and conducting detection focusing on characteristic X-rays. Concretely, the present inventors made the radiation detection element have a thickness that can detect characteristic X-rays sufficiently while allowing gamma rays to sufficiently pass through, and made each of the screening container and the collimator constituting a screening body have a thickness that screens out characteristic X-rays sufficiently while allowing gamma rays to sufficiently pass through. As a result, the present inventors succeeded in detecting presence of a radioactive substance with a screening body of one-eighteenth lighter than the conventional one by detecting characteristic X-rays while preventing the background. The "allow gamma rays to pass through" means that the proportion of the passing gamma rays in incident gamma rays is larger than those causing interaction. The "allow gamma rays to sufficiently pass through" means that 80% or more of gamma rays pass through, preferably 87% or more of gamma rays pass through, more preferably 92% or more of gamma rays pass through, and further preferably 97% or more of gamma rays pass through. Thickness of the radiation detection element means a thickness in the direction perpendicular to the plane where radiation enters into the radiation detection element (hereinafter, referred to as thickness in incident direction).

FIGS. 1A and 1B are graphs showing a simulation result of thickness of the radiation detection element and performance of the radiation detection element in the case where detection is conducted by characteristic X-rays having an energy of 32 keV and 36 keV radiated from cesium having a mass number of 137 (hereinafter $^{137}$Cs) and cesium having a mass number of 134 (hereinafter $^{134}$Cs). This simulation is based on the assumption that, with $^{137}$Cs and $^{134}$Cs placed on concrete present at a activity ratio of 1:0.9, the $^{137}$Cs and $^{134}$Cs are detected by characteristic X-rays in the environment that there are both gamma rays radiated from the two kinds of cesium and continuous gamma rays that are the gamma rays scattered by the concrete.

FIG. 1A represents a lower limit value $R_1$ of thickness of the radiation detection element, and FIG. 1B represents an upper limit value $R_2$ of thickness of the radiation detection element. In both graphs, the horizontal axis represents thickness (defined by mean free path λ) of the radiation detection element, and the vertical axis represents a value (hereinafter, $S^2/N$) obtained by standardizing a ratio between the square of detection efficiency (hereinafter S) of characteristic X-rays, and noise amount (N) given to the energy region (20-40 keV) of characteristic X-rays by gamma rays from $^{134}$Cs and $^{137}$Cs at the point where the thickness of the radiation detection element is 10 mm. In general, as $S^2/N$ increases, characteristic X-rays can be detected in a shorter time with higher accuracy, namely at higher sensitivity. Every graph shows the results using cesium iodide (hereinafter, CsI), cadmium telluride (hereinafter, CdTe), bismuth germanate (hereinafter, BGO), sodium iodide (hereinafter, NaI), and yttrium-aluminum-perovskite (hereinafter, YAP) as materials for the radiation detection element.

A micro amount of activation substance may be added to the scintillator for increasing the luminous efficiency. For example, CsI is not limited to pure CsI not containing an activation substance, but may be CsI (Na) or CsI (Tl) which is a scintillator to which a micro amount of sodium (Na) or thallium (Tl) is added as an activation substance. The activation substance will not be specifically described because the present invention is established regardless of presence or absence of an activation substance of the scintillator. In the aforementioned example, CsI means CsI not containing an activation substance, and CsI (Na) and CsI (Tl) containing an activation substance.

From the graph of FIG. 1A, it can be said that the radiation detection element preferably has a specific thickness. In other words, the lower limit value of the thickness of the radiation detection element (thickness of sensitive part), as shown as lower limit value R1 in FIG. 1A, is preferably $1.1\lambda_1$ or more in a unit of mean free path in the radiation detection element (in the substance) ($\lambda_1$) of characteristic X-rays from the radioactive substance to be measured. This value leads to 1.5 times efficiency of $S^2/N$ in the case of CsI.

The upper limit value of thickness of the radiation detection element (thickness of sensitive part), as shown as upper limit value R2 in FIG. 1B, is preferably $0.14\lambda_2$ or less in a unit of mean free path in the radiation detection element (in the substance) ($\lambda_2$) of the gamma rays that the radioactive substance to be measured radiates with the highest emission probability among all of the gamma rays with variety of energies from the radioactive substance. This value leads to 1.5 times efficiency of $S^2/N$ in the case of CsI.

The term "mean free path" means an average distance until characteristic X-rays or gamma rays cause interactions (photoelectric effect, Compton scattering, electron pair generation) after incidence to the substance (the same shall apply hereinafter).

From the view point of the proportion of characteristic X-rays that interact with the radiation detection element to total number of the incident characteristic X-rays, the thickness of the radiation detection element is preferably such that 67% or more of characteristic X-rays from the radioactive substance to be measured causes interaction after entering the detection element, and more preferably such that 78% or more of the characteristic X-rays causes interaction.

Further, from the view point of the proportion (hereinafter, transmittance) of gamma rays that completely fail to interact with the radiation detection element and pass through, the thickness of the radiation detection element preferably allows 87% or more of gamma rays with the highest emission probability among all of the gamma rays with variety of energies from the radioactive substance to be measured to pass through, and more preferably allows 95% or more of the gamma rays to pass through.

For example, in a conventional gamma camera, for imaging a radioactive substance with gamma rays with the highest emission probability from the radioactive substance to be measured, a very large thickness of the radiation detection element is required. In other words, in detecting gamma rays of 662 keV from $^{137}$Cs using NaI (diameter 50 mm) as the radiation detection element, for example, the conventional camera requires a thickness of about $0.81\lambda_2$ for obtaining a detection efficiency of 30%, and a larger thickness is required for further increasing the detection efficiency.

In contrast to this, the radiation detection element having a thickness of $0.14\lambda_2$ or less can operate in the present invention, and an efficiency of 80% or more can be easily obtained for characteristic X-rays. Therefore, it is possible to substantially reduce the weight of the radiation detection element.

Area (hereinafter, sensitive area) of the sensitive part of the radiation detection element per field of view defined by the collimator can be appropriate area depending on the intensity of incident characteristic X-rays. For example, in measuring a spent nuclear fuel substance at a close position in a nuclear facility or the like, it is preferred to make the sensitive area relatively narrow because the intensity of incident X-rays is large, whereas in measuring a radioactive fallout generated by a nuclear reactor accident or the like, it is preferred to increase the area to improve the sensitivity because the intensity of incident X-rays is small.

As to the sensitive area, for achieving a statistical error of 30% in a measuring time of 1 minute, the sensitive area is preferably at least 2 cm$^2$ or more, and the effective area may be 5 cm$^2$ or more, the effective area may be 12 cm$^2$ or more, or the effective area may be 96 cm$^2$ or more in conducting measurement in an environment where the air dose rate by gamma rays at the position of the radiation detection element CsI is less than 10 μSv/h.

Also, for example, in measuring in an environment where the air dose rate by gamma rays at the position of the radiation detection element CsI is less than 100 μSv/h, the sensitive area is preferably at least 0.3 cm$^2$ or more, and the effective area may be 1 cm$^2$ or more, the effective area may be 5 cm$^2$ or more, the effective area may be 12 cm$^2$ or more, or the effective area may be 96 cm$^2$ or more.

Similarly, in measuring in an environment where the air dose rate at the position of the radiation detection element CsI is less than X μSv/h, the sensitive area is preferably at least $(29 \times X^{-0.98})$ cm$^2$ or more (provided that, X>100 μSv/h). For other kinds of radiation detection elements, a sensitive area equivalent to that for CsI is required.

In the case where a longer measurement time and a larger statistical error are permitted, the sensitive area of the radiation detection element can be made smaller. The exemplified necessary sensitive area is approximately estimated based on the results of the radiation detection element CsI having an effective area of 16.6 cm$^2$, thickness of 1 mm, and energy resolution of 10.5 keV at 32 keV, measured in environments where the air dose rate by gamma rays at the CsI position is 5 μSv/h and 16 μSv/h.

Figure 2B:
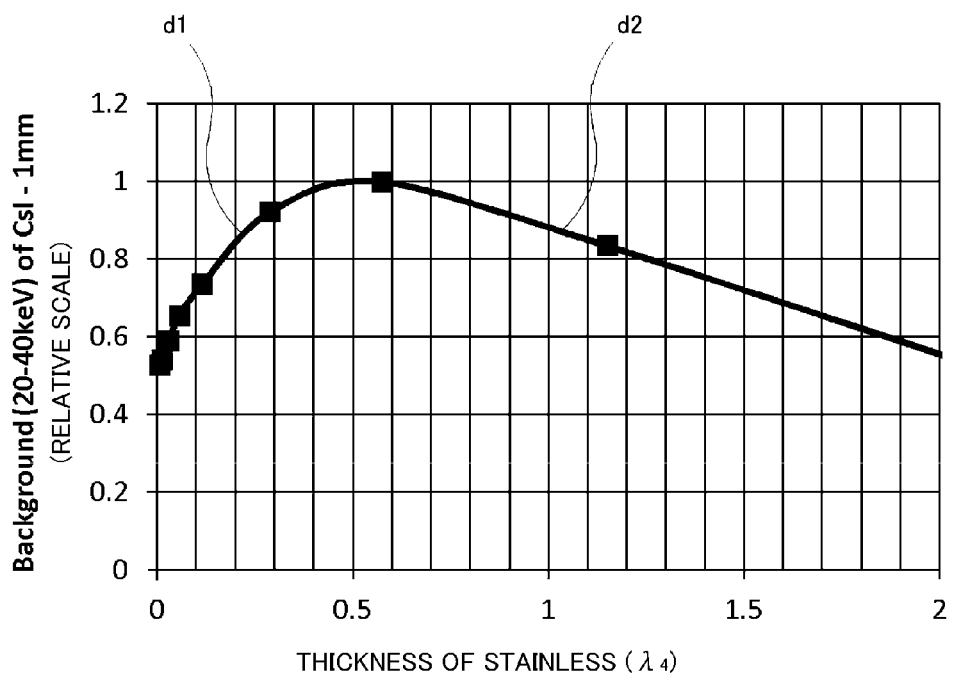

FIGS. 2A and 2B are explanatory charts for explaining various changes due to change in thickness of the screening container, and FIG. 2A is a graph showing the relation between the thickness of the screening container, the screen factor of characteristic X-rays, and the transmittance of gamma rays. Thickness of the screening container means the thickness of a wall of a container having one open end and the other closed end. This graph is calculated by using stainless (hereinafter SUS) as a material for the screening container. Here, the characteristic X-rays to be screened out are characteristic X-rays of 32 keV radiated from cesium $^{137}$Cs, and the gamma rays to be allowed to pass through is gamma rays of 662 keV radiated from $^{137}$Cs.

The horizontal axis of the graph represents thickness of the screening container. The vertical axis of the graph represents screen factor of characteristic X-rays, and transmittance of gamma rays.

As shown in the drawing, the screening level of characteristic X-rays by the screening container is about 40% at a thickness of the screening container of 0.1 mm, and increases with the thickness of the screening container, and almost 100% (98% in calculation example) screening can be achieved at a thickness of 1 mm.

On the other hand, transmittance of gamma rays is about 60% when the thickness of the screening container is 10 mm, and it increases as the thickness of the screening container is reduced, and is about 90% at a thickness of 2 mm.

From these results, when SUS is selected as a material, thickness of the screening container is most preferably 1 mm. That is, this thickness can screen out nearly 100% (98%) of characteristic X-rays of 32 keV, allows gamma rays to pass through, and can reduce the weight of the screening container. By employing such a thickness that allows gamma rays to pass through, reduces the weight, and can sufficiently screen out characteristic X-rays, it is possible to make the screening container very light, and to obtain sufficient detection accuracy.

More specifically, thickness of the screening container is preferably $1.6\lambda_3$ or more in a unit of mean free path ($\lambda_3$) of characteristic X-rays from the radioactive substance to be measured in the screening container, and is preferably $0.22\lambda_4$ or less in a unit of mean free path ($\lambda_4$) of the gamma ray radiated with the highest emission probability from the radioactive substance to be measured in the screening container.

Thickness of the screening container preferably screens out 80% or more of characteristic X-rays having an energy of 20 keV to 40 keV, and more preferably screens out 90% or more of the characteristic X-rays, from the view point of screening out characteristic X-rays.

Thickness of the screening container desirably allows 80% or more of gamma rays radiated with the highest emission probability from the radioactive substance to be measured to pass through for reducing the weight of the screening container, preferably allows 87% or more of the gamma rays to pass through, more preferably allows 92% or more of the gamma rays to pass through, and further preferably allows 97% or more of the gamma rays to pass through from the view point of transmittance of gamma rays.

For example, in a conventional gamma camera, for imaging a radioactive substance by gamma rays that are radiated with the highest emission probability from the radioactive substance to be measured, it is necessary to make thickness of the screening container about $4\lambda_4$ for screening out 98% of gamma rays. In contrast to this, since the screening container having a thickness of $0.22\lambda_4$ or less can operate in the present invention, it is possible to substantially reduce the weight of the screening container to one-eighteenth or less. The screening container of such a thickness reduces the weight of the screening container and detects characteristic X-rays with high accuracy, so that a radioactive substance detection device having light weight and high sensitivity can be provided.

Achievement of both weight reduction of the screening container and sensitivity improvement by setting the thickness of the screening container at $0.22\lambda_4$ or less in this manner will be described using an example in which SUS is used for the screening container by referring to FIG. 2B. FIG. 2B is a graph obtained by calculating the relation between thickness of SUS (in a unit of mean free path $\lambda_4$ in SUS of 662 keV) and background amount of 20-40 keV detected by CsI when both surfaces of the radiation detection element CsI having a thickness of 1 mm are screened out by SUS of the same thickness, and one surface of SUS is irradiated with gamma rays of 662 keV from a radiation source $^{137}$Cs. This graph gives an indication of the relation between thickness of the screening container and background amount in the condition that there is no matter around the radiation source.

As shown in this graph, the background peaks at a thickness of SUS of about $0.5\lambda_4$. Therefore, decreasing the thickness of the screening container to $0.22\lambda_4$ or less which is thin enough to reduce the background is effective for reducing the background as well as for reducing the weight. To be more specific, the background can be reduced to 87% of the maximum value when the thickness of the screening container is $0.22\lambda_4$ (d1 in the drawing) and when the thickness of the screening container is $1.03\lambda_4$ (d2 in the drawing). That is, the points (for example, d1 and d2) appear where the background can be reduced by an equal amount on the thinner side and on the thicker side with respect to the thickness of the screening container where the background amount is maximum. However, about 4.7 times weight reduction is achieved with the same background amount in the condition of d1 situated on the thinner side, than in the condition of d2 situated on the thicker side.

Such a way of thinking for thickness of the screening container is also applied to design of the collimator, and it is preferred to make the collimator to have a specific thickness.

In general, a collimator is formed of a plate-like member having holes, and when it is attached to the screening container, it allows most of incident radiation and so on from a specified direction to pass through the holes, and excludes most of incident radiation and so on from directions other than the specified direction by the member around the holes. In other words, the field of view is limited by the collimator. In the case of X-rays and gamma rays, the thickness (effective thickness) of the collimator is one parameter determining the field of view of the collimator. Here, the specified direction is a direction in which measurement is to be made, and is a direction defined by the collimator and the screening container, or a direction defined by the screening container.

The collimator includes the type provided with one radiation detection element behind the collimator, and the type provided with a plurality of radiation detection elements.

Figure 5A:
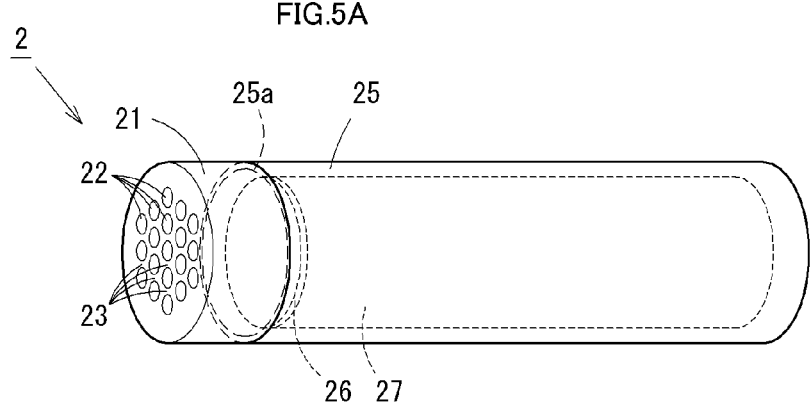
FIGS. 5A to 5C are explanatory views for explaining a constitution of a radioactive substance detection device.
Figure 5B:
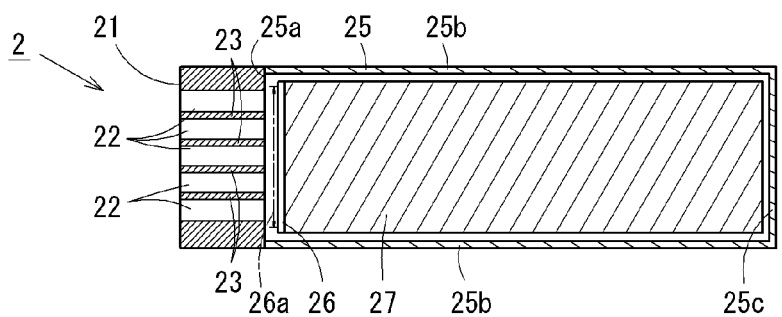
Figure 12:
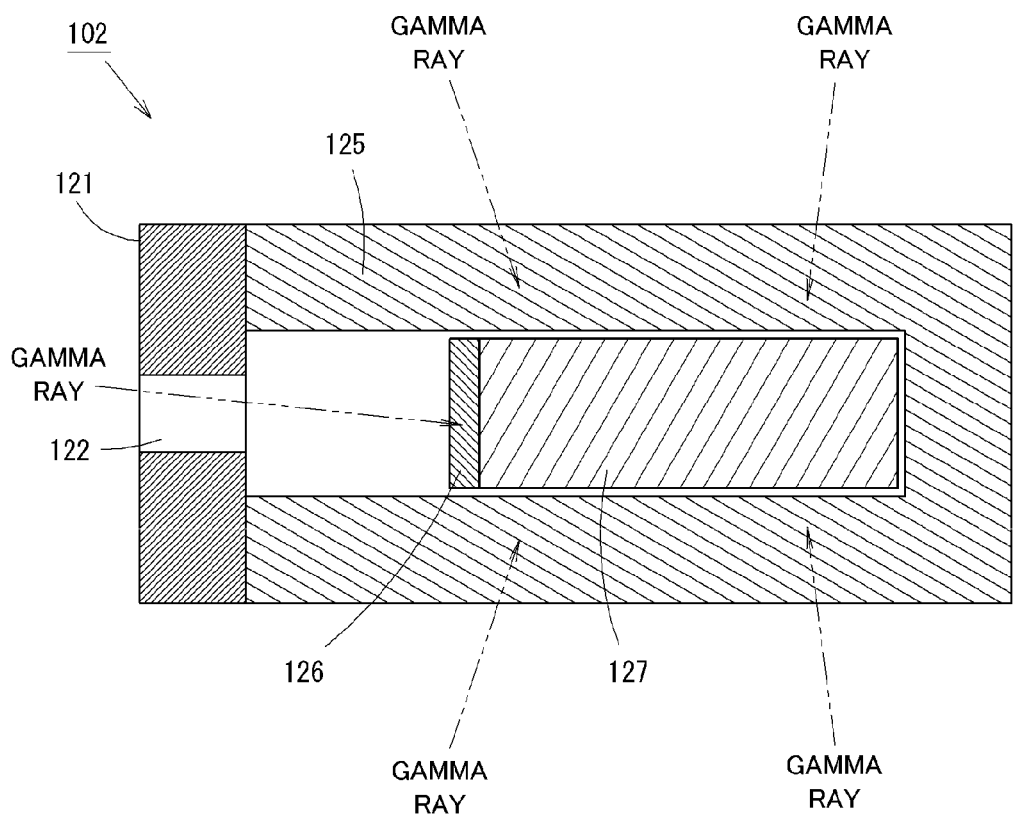
FIG. 12 is a longitudinal section view showing a conventional radiation measurement device.

Examples of the former type include a single collimator having one hole (see single collimator 121 in FIG. 12) and a multiple collimator having a plurality of holes (see collimator 21 in FIGS. 5A and 5B). The effective thickness means thickness of the lateral wall of a hole in the single collimator or in the multiple collimator. In other words, it is an average of thicknesses (wall thickness in the direction perpendicular to the specified direction) of collimator member at the point where radiation from arbitrary directions enters in the collimator member (excluding the cases where incidence occurs in the front face or the back face on the specified direction side of the collimator).

Examples of the latter type include a pinhole collimator and a coded mask type collimator and so on as will be described later. In a pinhole collimator or a coded mask type collimator, effective thickness means a plate thickness of the collimator. In other words, it is an average of thickness (wall thickness in the direction parallel to the specified direction) of collimator member at the point where radiation from arbitrary directions enters in the collimator member (excluding the cases where incidence occurs on the lateral wall of a hole or outer circumferential face of the collimator).

Effective thickness of the collimator is $1.6\lambda_5$ or more in a unit of mean free path in the collimator substance ($\lambda_5$) of characteristic X-rays from the radioactive substance to be measured, and is preferably $0.22\lambda_6$ or less in a unit of mean free path in the collimator substance ($\lambda_6$) of gamma rays radiated with the highest emission probability from the radioactive substance to be measured.

Effective thickness of the collimator preferably screens out 80% or more of characteristic X-rays having an energy of 20 keV to 40 keV, and more preferably screens out 90% or more of the characteristic X-rays from the view point of screening out the characteristic X-rays.

From the view point of transmittance of gamma rays, effective thickness of the collimator preferably allows 80% or more of the gamma rays with the highest emission probability from the radioactive substance to be measured to pass through for reducing the weight of the screening container, and preferably allows 87% or more of the gamma rays to pass through, more preferably allows 92% or more of the gamma rays to pass through, and further preferably allows 97% or more of the gamma rays to pass through.

For example, in a conventional gamma camera, for imaging a radioactive substance with gamma rays with the highest emission probability from a radioactive substance to be measured, a large effective thickness of the collimator is required. That is, the conventional gamma camera requires an effective thickness of the collimator of about $4\lambda_6$ for determining the arriving direction of gamma rays with an accuracy of 98%.

In contrast to this, since the collimator having an effective thickness of $0.22\lambda_6$ or less can operate in the present invention, it is possible to substantially reduce the weight of the collimator.

The signal processing circuit provided on the rear stage of the radiation detection element is preferably configured to measure a spectrum near a peak of characteristic X-rays radiated from the radioactive substance over at least part of the range from 20 keV to 40 keV, and is more preferably configured to measure over at least the entire range of 20 keV to 40 keV, and for evaluating a peak of characteristic X-rays more accurately, it is preferably configured to measure over the entire range of 10 keV to 40 keV and is more preferably configured to measure over the entire range of 10 keV to 50 keV. In particular, by a signal processing circuit capable of measuring down to 10 keV, the estimation accuracy of background increases, and peak analytical accuracy is improved. Also, by a signal processing circuit capable of measuring up to 50 keV, it is possible to further increase the accuracy.

For example, when $^{137}$Cs is to be detected, it is desired to be configured to measure a spectrum around 32.2 keV (Ba—K$\alpha$) and 36.4 keV (Ba—K$\beta$) which are peaks of characteristic X-rays radiated during a process that $^{137}$Cs $\beta^-$-decays to $^{137m}$Ba and then decays to $^{137}$Ba by nuclear isomer transition.

For example, when $^{131}$I is to be detected, it is desired to be configured to measure a spectrum around 29.8 keV (Xe—K$\alpha$) and 33.6 keV (Xe—K$\beta$) which are peaks of characteristic X-rays radiated during a process that $^{131}$I $\beta^-$-decays to $^{131m}$Xe and then decays to $^{131}$Xe by nuclear isomer transition.

For example, when $^{129m}$Te is to be detected, it is desired to be configured to measure a spectrum around 27.5 keV (Te—K$\alpha$) and 31.0 keV (Te—K$\beta$) which are peaks of characteristic X-rays radiated during a process that $^{129m}$Te decays to $^{129}$Te by nuclear isomer transition.

For example, when $^{132}$Te is to be detected, it is desired to be configured to measure a spectrum around 28.6 keV (I—K$\alpha$) and 32.3 keV (I—K$\beta$) which are peaks of characteristic X-rays radiated during a process that $^{132}$Te decays to $^{132}$I by $\beta^-$-decay.

For example, when $^{133}$Ba is to be detected, it is desired to be configured to measure a spectrum around 31.0 keV (Cs—K$\alpha$) and 35.0 keV (Cs—K$\beta$) which are peaks of characteristic X-rays radiated during a process that $^{133}$Ba decays to $^{133}$Cs by electron capture.

For example, when $^{124}$I is to be detected, it is desired to be configured to measure a spectrum around 27.5 keV (Te—K$\alpha$) and 31.0 keV (Te—K$\beta$) which are peaks of characteristic X-rays radiated during a process that $^{124}$I $\beta^+$-decays to $^{124}$Te or decays by electron capture.

Therefore, by employing the configuration of measuring at least part of the range from 20 keV to 40 keV, it is possible to detect and analyze peaks of the characteristic X-rays radiated from these radioactive substances.

Next, a method for identifying the kind of radioactive substances will be described. For those radiating both gamma rays and characteristic X-rays during the process that a radioactive substance (parent nuclide) decays to a daughter nuclide, the present invention makes it possible to detect a radioactive substance being present in a specified direction using characteristic X-rays detected in a low energy region (X-ray region of for example, from 10 keV to 50 keV), and to identify the kind of the radioactive substance (atomic number of daughter nuclide) in that direction. Furthermore, by additionally using detection of radiation in the high energy region (gamma ray area of, for example, 60 keV to 1,000 keV), it is possible to identify the kind of the radioactive substance being present in the specified direction more specifically. This will be described in detail below.

Figure 3A:
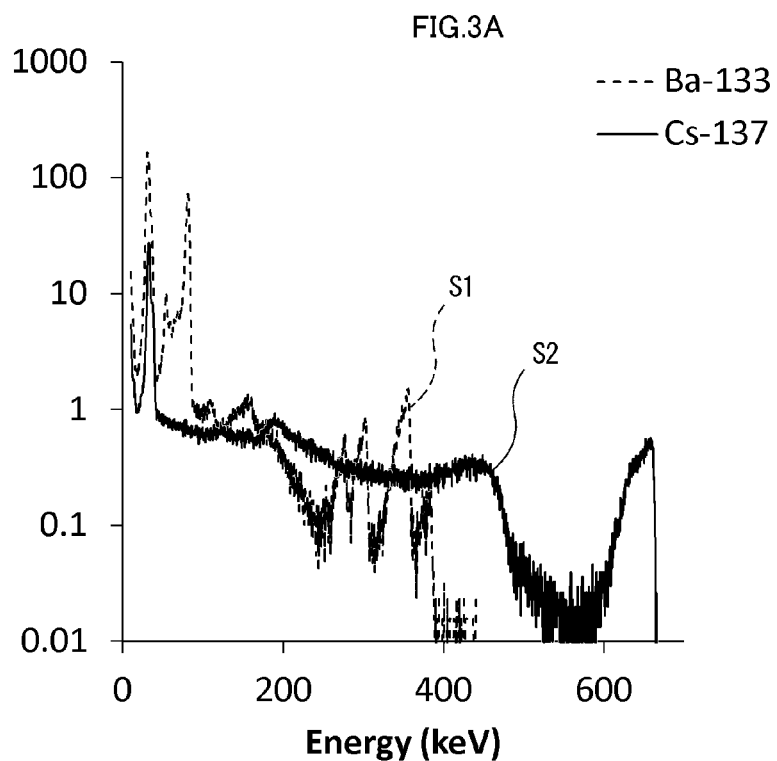
FIGS. 3A and 3B are explanatory charts of an energy spectrum of a radioactive substance for use in identifying the kind of the radioactive substance.
Figure 3B:
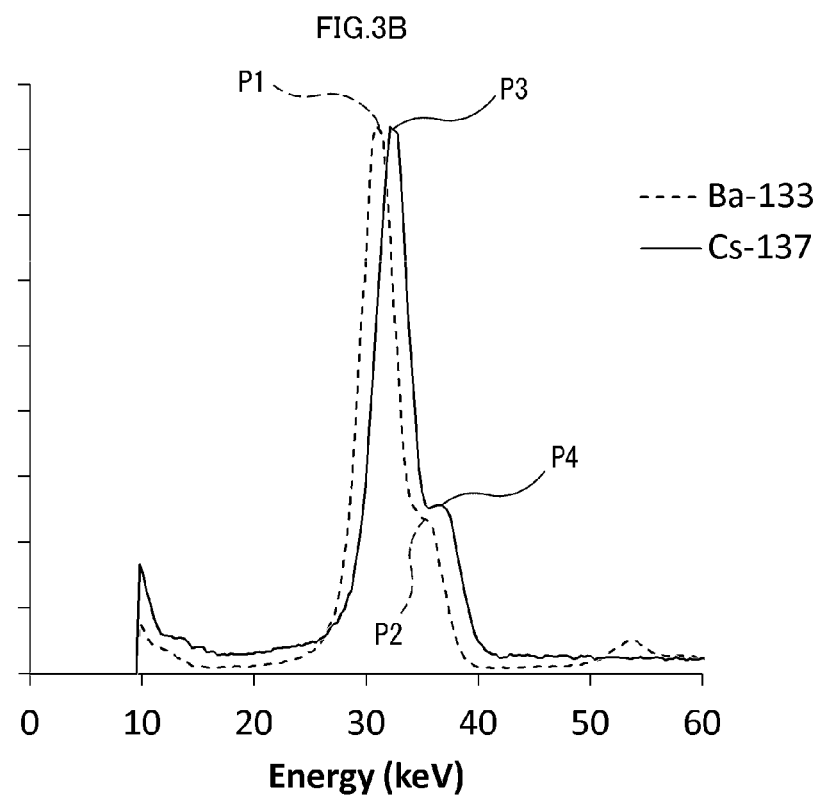

FIG. 3A shows energy spectra spanning 0 to 700 keV of $^{133}$Ba and $^{137}$Cs measured by using cadmium telluride as the radiation detection element at $-10°$ C., and FIG. 3B shows the characteristic X-rays spanning 0 to 60 keV in FIG. 3A in such a manner that the heights of respective peaks are aligned. In FIGS. 3A and 3B, the vertical axis represents count, and the horizontal axis represents energy (keV).

Energy resolution of the cadmium telluride element used herein is 4 keV at an energy of 32 keV when defined by full width at half maximum.

First, the first method of radioactive substance identification in specified direction will be described that uses a low energy region radioactive substance identification method for identifying the kind of the radioactive substance (atomic number of daughter nuclide) being present in a specified direction using radiation in a low energy region. The low energy region radioactive substance identification method is executed as a daughter nuclide identification process for identifying the atomic number of the daughter nuclide of the radioactive substance being present in the specified direction.

As shown in FIG. 3B, in the low energy region, peak P1 (31 keV) and peak P2 (35 keV) of the characteristic X-ray of Cs occurring in association with decay of $^{133}$Ba (daughter nuclide $^{133}$Cs), and peak P3 (32 keV) and peak P4 (36 keV) of the characteristic X-ray of Ba occurring in association with decay of $^{137}$Cs (daughter nuclide $^{137}$Ba) arise.

Small difference between positions of peaks P1, P2 of the characteristic X-ray occurring in association with decay of $^{133}$Ba and positions of peaks P3, P4 of the characteristic X-ray occurring in association with decay of $^{137}$Cs is ascribable to difference in energy between these characteristic X-rays. By knowing positions of the energy peaks, it is possible to identify the atomic number of the daughter nuclide of the radioactive substance. That is, energy of a characteristic X-ray depends exclusively on atomic number of a daughter nuclide that is generated by decay of a radioactive substance (parent nuclide). Daughter nuclides of $^{133}$Ba and $^{137}$Cs after decay are $^{133}$Cs and $^{137}$Ba, respectively, and characteristic X-rays (those having the highest intensities: 31 keV, 32 keV, respectively) corresponding to the atomic numbers of the daughter nuclides (Cs, Ba, respectively) will occur. Therefore, conversely, by measuring energy of a characteristic X-ray, it is possible to know an atomic number of a daughter nuclide. Although it is generally impossible to know a parent nuclide from an atomic number of a daughter nuclide, it is possible to limit the kinds of parent nuclides.

Since the radiation detection element is surrounded by the screening body (the screening container and the collimator, or the screening container in the case of lacking a collimator), the detected characteristic X-rays come from a radioactive substance being present in the specified direction. Therefore, it is possible to identify the kind of the radioactive substance (atomic number of the daughter nuclide) being present in the specified direction from the position of the peak of the characteristic X-ray in the low energy region.

By improving the energy resolution of the radiation detection element, the ability to identifying the kind of the radioactive substance (atomic number of daughter nuclide) can be improved. For example, in the case of cadmium telluride, it is possible to improve the energy resolution to 1 keV or less by the methods of, for example, cooling cadmium telluride to further low temperature, optimizing the size of cadmium telluride, or using a pre-amplifier having more excellent noise performance. The cooling is a method for increasing the energy resolution and is not an essential requirement. Even when the cadmium telluride is used at room temperature (for example, at 20° C.), it is possible to discriminate difference in peak position and to identify an atomic number of a daughter nuclide of a radioactive substance.

Next, a high energy region radioactive substance identification method (identification method of kind (kind of parent nuclide) of radioactive substance using radiation in the high energy region) will be described in which presence of a radioactive substance in the vicinity of radioactive substance detection device is recognized using radiation in the high energy region to identify the kind (kind of parent nuclide).

In the present invention, the thickness of the radiation detection element is set at such a thickness that allows gamma rays to sufficiently pass through and can sufficiently detect characteristic X-rays. The thickness of the screening body is set at such a thickness that allows gamma rays to sufficiently pass through and sufficiently screens out characteristic X-rays. Therefore, most of gamma rays in the high energy region pass through the screening body, and arrive from every direction to enter the radiation detection element. Although most of gamma rays in the high energy region pass through the radiation detection element, part of them interact with the radiation detection element and are detected. The data of detection of the part of gamma rays is utilized for identifying the kind of the radioactive substance (kind of parent nuclide).

In identification of the kind of the radioactive substance (kind of parent nuclide) using gamma rays in the high energy region, since gamma rays arriving from every direction are to be detected, it is to be noted that the incident directions of gamma rays can not be identified. That is, it is to be noted that the radioactive substances that can be identified by the high energy region of energy spectra include those being present in the region of the specified direction where a radioactive substance can be detected by characteristic X-rays, and those being present in other region (region where characteristic X-rays are screened out by the screening body, and detection is not conducted by characteristic X-rays).

In the high energy region, as shown in FIG. 3A, gamma rays that slightly interact with cadmium telluride form energy spectra S1, S2. The energy spectrum S1 of $^{133}$Ba and the energy spectrum S2 of $^{137}$Cs are different in shape. The energy spectra S1, S2 are inherent in the radioactive substances, and depend on energy of gamma rays radiated from the respective radioactive substances.

Therefore, by observing the shape of the energy spectrum in the high energy region, it is possible to recognize presence of a radioactive substance in the vicinity of the radioactive substance detection device and to identify the kind (kind of parent nuclide). That is, in the high energy region, the direction in which a radioactive substance is present cannot be identified, but the kind (kind of parent nuclide) of the radioactive substance being present in the vicinity can be identified. Concretely, templates of individual parent nuclides registered in a database (data regarding peak) and the shape of the energy spectrum in the high energy region are compared, and if there is a template indicating a degree of coincidence of a predetermined value or more, the kind of the radioactive substance is identified as the parent nuclide with the template.

Further, the second method of radioactive substance identification in specified direction will be described in which energy and intensity of characteristic X-rays are estimated by a characteristic X-ray peak estimation method using the result of the kind of the radioactive substance (kind of parent nuclide) identified by the high energy region radioactive substance identification method, and the kind of the radioactive substance being present in the specified direction (kind of parent nuclide) is identified by a low energy region radioactive substance detailed identification method using the estimation result. The high energy region radioactive substance identification method is executed as a candidate identification process for identifying a candidate for the radioactive substance being present in the specified direction, and the characteristic X-ray peak estimation method and the low energy region radioactive substance detailed identification method are executed as a kind discrimination process for discriminating the kind of radioactive substance being present in the specified direction using the identification result by the high energy region radioactive substance identification method and the measurement result of the low energy region.

Respective energy of characteristic X-rays or gamma rays and a radiation ratio between gamma rays and characteristic X-rays are inherent in the radioactive substance. Also, the detection efficiency of gamma rays and characteristic X-rays are inherent in the radioactive substance detection device. The characteristic X-ray peak estimation method estimates energy and intensity of characteristic X-rays utilizing this law.

In the characteristic X-ray peak estimation method, first, using the aforementioned high energy region radioactive substance identification method, presence of each radioactive substance in the vicinity of the radioactive substance detection device is recognized from a gamma ray spectrum in the high energy region. For this recognized radioactive substance, energy of each characteristic X-ray is determined, and based on the radiating ratio between gamma rays and characteristic X-rays, the detection efficiency of gamma rays and characteristic X-rays, and assumption of distribution condition of radioactive substance, intensity of each characteristic X-ray by each radioactive substance is estimated.

For example, the case where measurement is conducted in the field where two kinds of radioactive substances, $^{133}$Ba and $^{137}$Cs coexist is supposed. From a gamma ray spectrum of the high energy region, presences of the radioactive substances $^{133}$Ba and $^{137}$Cs in the vicinity of the radioactive substance detection device are recognized, and energy and intensity of the characteristic X-rays radiated from the two kinds of the radioactive substances are estimated. In other words, for the radioactive substances $^{133}$Ba and $^{137}$Cs whose presences have been recognized, an assumption is made that for example, the radioactive substances are uniformly distributed on the ground surface, and energy of characteristic X-ray radiated from each substance is extracted from a known database. And further an operation using a radiation ratio between gamma rays and characteristic X-rays and detection efficiency of gamma rays and characteristic X-rays is conducted to estimate intensity of each characteristic X-ray.

Next, based on the estimation, a characteristic X-ray spectrum of the low energy region is analyzed using a low energy region radioactive substance detailed identification method. The low energy region radioactive substance detailed identification method will be described while taking the field where two kinds of radioactive substances $^{133}$Ba and $^{137}$Cs coexist as an example. By actively searching peaks of characteristic X-rays having the estimated energy and intensity (characteristic X-ray peaks of Cs being daughter nuclide of $^{133}$Ba and of Ba being daughter nuclide of $^{137}$Cs) from the low energy region (if there is a peak within an acceptable range confined by the estimated energy and intensity of characteristic X-ray, the peak is regarded as that of the characteristic X-ray), it is possible to determine presence or absence of each peak of characteristic X-rays, and intensities of each peak accurately, and to determine whether or not the radioactive substance of the kind specified in the high energy region radioactive substance identification method is present in the low energy region. When presence is determined, it is identified that the radioactive substance of that kind is present in the specified direction.

The second method of radioactive substance identification in specified direction that analyzes the low energy region by combining the high energy region radioactive substance identification method, the characteristic X-ray peak estimation method, and the low energy region radioactive substance detailed identification method in this manner is particularly useful when the energy resolution of the radioactive detection element is comparable to difference in characteristic X-ray energies of each radioactive substance. To be more specific, in the example of the field where two kinds of radioactive substances $^{133}$Ba and $^{137}$Cs coexist as described above, energy difference in characteristic X-rays is 1 keV. Meanwhile, characteristic X-ray peaks are close to each other as shown in FIG. 3B, and are actually observed as a single peak. The abundance and the kind of the parent nuclide are not clear only from information of the spectrum of the low energy region. Therefore, it is difficult to recognize characteristic X-ray peaks of two kinds Cs and Ba derived from $^{133}$Ba and $^{137}$Cs, and to separate them from each other. Instead, by identifying the kind of the radioactive substance ($^{133}$Ba and $^{137}$Cs) from the high energy region, it is possible to estimate the energy and the intensity of the characteristic X-ray, and to detect characteristic X-rays of $^{133}$Ba and $^{137}$Cs while separating them from each other, and to achieve high accuracy measurement of characteristic X-ray intensity. In this case, it is possible to quantify $^{133}$Ba and $^{137}$Cs independently, and to identify the radioactive substances (parent nuclide) being present in the specified direction as being $^{133}$Ba and $^{137}$Cs.

The second method of radioactive substance identification in specified direction is able to identify the kind of the radioactive substance being present in the specified direction better than in the first method of radioactive substance identification in specified direction using only the low energy region radioactive substance identification method, by using a gamma ray spectrum of the high energy region even when energy resolution is poor. That is, in the field of the aforementioned case where $^{133}$Ba and $^{137}$Cs coexist, although the atomic number of daughter nuclide can be identified from the information of the low energy region used in the first method of radioactive substance identification in specified direction, it is just limitation to a certain width (for example, daughter nuclide is limited to Xe, Cs, Ba, La) because an error occurs depending on the degree of the energy resolution. However, in the second method of radioactive substance identification in specified direction, by measuring a gamma ray spectrum of the high energy region by the aforementioned high energy region radioactive substance identification method, it is possible to identify either one or both of $^{133}$Ba and $^{137}$Cs as candidates for the radioactive substance being present in the specified direction.

When the energy resolution is excellent, it is possible to realize the second method of radioactive substance identification in specified direction that identifies the kind (parent nuclide) of the radioactive substance being present in the region of the specified direction by the low energy region radioactive substance detailed identification method that combines the result of energy and intensity of characteristic X-ray estimated by the aforementioned high energy region radioactive substance identification method and the characteristic X-ray peak estimation method, and a measurement result of energy spectrum of characteristic X-ray in the low energy region. That is, in the field where $^{133}$Ba and $^{137}$Cs coexist, it is possible to identify the atomic number of daughter nuclide of the radioactive substance as Cs and Ba from the low energy region, and to identify that $^{133}$Ba and $^{137}$Cs are present in the vicinity of the radioactive substance detection device from the gamma ray spectrum of the high energy region, so that the two low energy characteristic X-ray peaks can be recognized as being derived from $^{133}$Ba and $^{137}$Cs. Therefore, it is possible to identify the kind (kind of parent nuclide) of the radioactive substances being present in the specified direction as being $^{133}$Ba and $^{137}$Cs.

In the aforementioned example, two kinds of radioactive substances ($^{133}$Ba and $^{137}$Cs) are present and their daughter nuclides ($^{133}$Cs and $^{137}$Ba, respectively) have different atomic numbers. In this case, if the energy difference in characteristic X-rays is comparable to or larger than the energy resolution of the radiation detection element, it is possible to identify the kind of the radioactive substance being present in the specific region ($^{133}$Ba and $^{137}$Cs in this example), detect the respective quantities separately, and measure them independently.

On the other hand, for example, in the example where $^{137}$Cs and $^{134}$Cs (their daughter nuclides are $^{137}$Ba and $^{134}$Ba, respectively) coexist, the atomic number of their daughter nuclides are identical, and these radiate characteristic X-rays of the same energy, so that it is impossible to identify the kind (kind of parent nuclide) of the radioactive substance being present in the specific region, detect the respective quantities separately, and quantify them independently. However, by conducting the second method of radioactive substance identification in specified direction using the gamma ray spectrum of the high energy region, it is possible to identify better than in the case where only the characteristic X-ray spectrum of the low energy region is used (the first method of radioactive substance identification method of specified direction by the low energy region radioactive substance identification method). In other words, the first method of radioactive substance identification in specified direction by the low energy region radioactive substance identification method can merely confirm that the daughter nuclide of the radioactive substance being present in the specified direction is Ba, but in the second method of radioactive substance identification in specified direction using information of the high energy region, it is possible to identify the kind (kind of parent nuclide) of the radioactive substance as being both of or either one of $^{137}$Cs and $^{134}$Cs.

When only one kind of radioactive substance is present in the vicinity of the radioactive substance detection device, it is possible to identify the kind (kind of parent nuclide) of the radioactive substance from the gamma ray spectrum of the high energy region by using the second method of radioactive substance identification in specified direction, and since the characteristic X-rays detectable in the low energy region are apparently radiated from the radioactive substance, it is possible to identify the kind (kind of parent nuclide) of the radioactive substance being present in the region of the specified direction.

In the field where three or more kinds of radioactive substances coexist, it is possible to identify the kind (kind of parent nuclide) of radioactive substance being present in the vicinity of the radioactive substance detection device from the gamma ray spectrum of the high energy region by using the high energy region radioactive substance identification method. If their daughter nuclides have different atomic numbers and difference in energy of their characteristic X-ray is comparable or superior to the energy resolution of the radiation detection element, it is possible to identify the kind of radioactive substance being present in the region of the specified direction by the second method of radioactive substance identification in specified direction. If some of their daughter nuclides have the same atomic number, it is impossible to identify the kind (kind of parent nuclide) of radioactive substance being present in the specific region, to detect respective quantities separately, and to quantify them independently. However, in the second method of radioactive substance identification in specified direction, it is possible to limit the kind (kind of parent nuclide) of radioactive substance being present in the region of the specified direction by using the gamma ray spectrum of the high energy region, and to identify better than by the first method of radioactive substance identification in specified direction using only the characteristic X-ray spectrum of the low energy region.

As described above, it is possible to identify the atomic number of the daughter nuclide of the radioactive substance being present in the specified direction from the low energy region (the first method of radioactive substance identification in specified direction by the low energy region radioactive substance identification method). Further, by analyzing a peak of the radioactive substance in the low energy region based on the estimation using the detection result of the high energy region, it is possible to measure the characteristic X-ray intensity of the radioactive substance more accurately, and to discriminate the kind (kind of parent nuclide) of radioactive substance being present in the specified direction (the second method of radioactive substance identification in specified direction using the high energy region and the low energy region).

It is also operable as a simplified air dosimeter by calculating the energy amount absorbed to the radiation detection element from the energy spectrum using both the spectrum of the low energy region (spectrum of characteristic X-ray region) and the spectrum of the high energy region (gamma ray spectrum of the high energy region).

In this manner, it is possible to provide a radioactive substance detection device that detects a radioactive substance accurately, identifies the kind of the radioactive substance, and is very light in weight.

One embodiment of the present invention will be described below together with drawings.

First Embodiment

Figure 4:
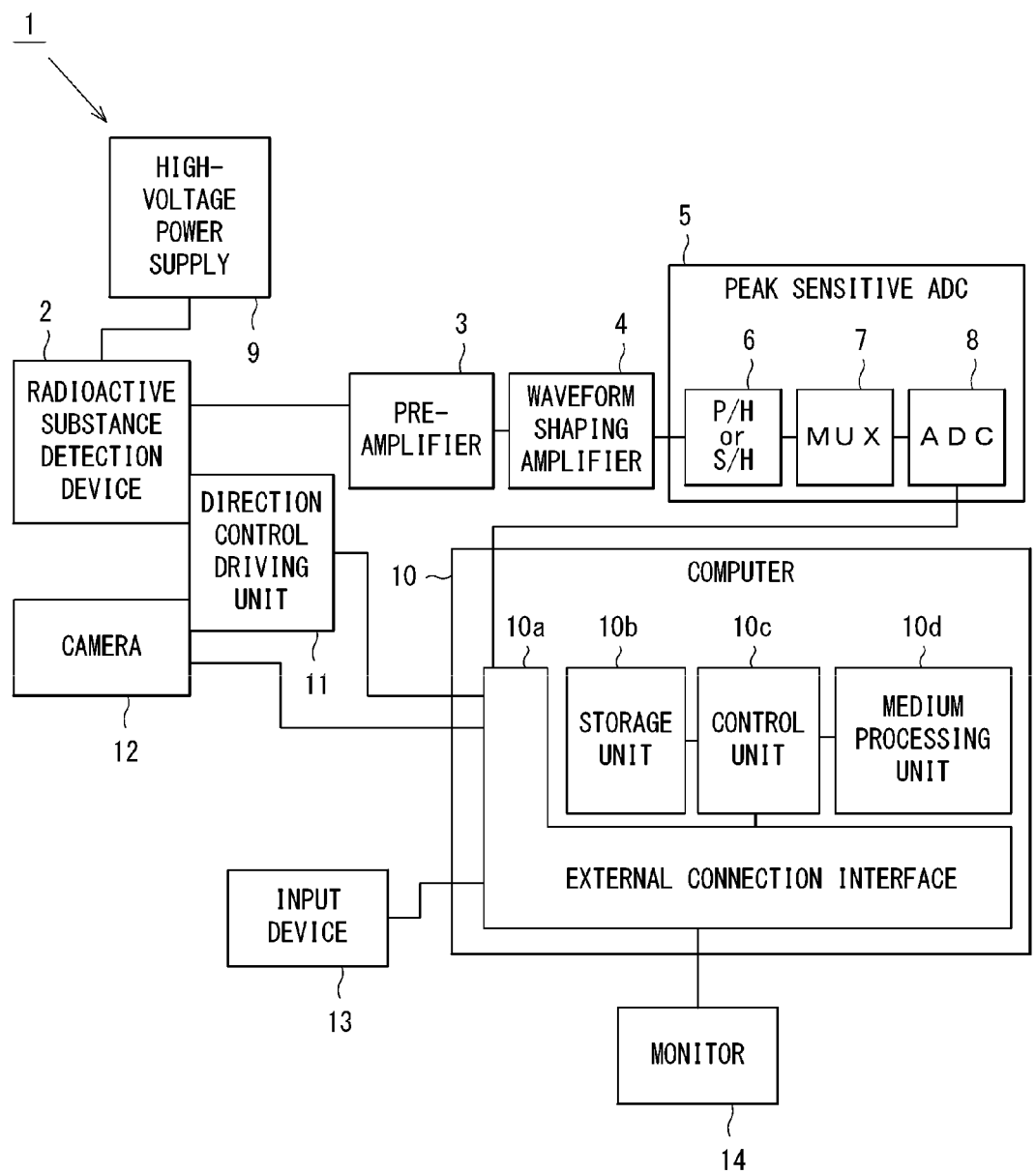
FIG. 4 is a block diagram showing a system configuration of a radiation source location visualization system.

FIG. 4 is a block diagram showing a system configuration of a radiation source location visualization system 1.

The radiation source location visualization system 1 includes a radioactive substance detection device 2, a pre-amplifier 3, a waveform shaping amplifier 4, a peak sensitive ADC 5 (a sample-and-hold circuit or peak-hold circuit 6, (a multiplexer 7), ADC 8), a high-voltage power supply 9, a computer 10, a direction control driving unit 11, a camera 12, an input device 13, and a monitor 14. The illustrated radiation source location visualization system 1 shows an example of a single elemental module.

The radioactive substance detection device 2 is a device that detects a radioactive substance by detecting characteristic X-rays, and operates under power supply from the high-voltage power supply 9. A signal measured in the radioactive substance detection device 2 is transmitted to the pre-amplifier 3 of rear stage.

The pre-amplifier 3 amplifies a received signal.

The waveform shaping amplifier 4 is embodied by a high-pass filter and/or a low-pass filter, and shapes the waveform of a signal received from the pre-amplifier 3 and transmits the signal to the peak sensitive ADC 5 of rear stage. As a result, it is possible to narrow down the bandwidth of the signal to be detected, and to remove noises.

The peak sensitive ADC 5 is also called a peak sensing ADC, and detects a peak (maximum value of analogue wave height) of signal received from the waveform shaping amplifier 4 by the sample-and-hold circuit or peak-hold circuit 6, and converts the signal to a digital signal (digital numerical value) by the ADC 8, and transmits the digital signal to the computer 10 of rear stage. Between the sample-and-hold circuit or peak-hold circuit 6 and the ADC 8, the multiplexer 7 is provided if it is necessary. To this multiplexer 7, other devices are connected to the input if it is necessary.

The high-voltage power supply 9 supplies the radioactive substance detection device 2 with high voltage power required for operation of the radioactive substance detection device 2.

The computer 10 includes an external connection interface 10a such as a USB port and a serial port for connection of an external device, a storage unit 10b embodied by a hard disc or a flash memory, a control unit 10c having CPU ROM and RAM, and a storage medium processing unit 10d for conducting reading/writing from/to a storage medium such as CD-ROM.

To the computer 10, the peak sensitive ADC 5, the direction control driving unit 11, the camera 12 for acquiring a still image, the input device 13 embodied by a mouse and a keyboard or a touch panel or the like, for accepting operation input by a user, and the monitor 14 embodied by a liquid crystal display or a CRT display, for displaying an image are connected. The direction control driving unit 11 drives to control the directions of the radioactive substance detection device 2 and the camera 12. In this control driving, the direction control driving unit 11 controls so that the radioactive substance detection device 2 and the camera 12 are directed in the same direction.

In the computer 10, according to the program stored in the storage unit 10b, the control unit 10c executes various operations and operation controls of various devices, and executes counting, image processing and so on of a digital signal received from the peak sensitive ADC 5. The details will be described later.

The signal processing in the radioactive substance detection device 2, the pre-amplifier 3, the waveform shaping amplifier 4, and the peak sensitive ADC 5 is configured to be able to detect characteristic X-ray peaks of 20-40 keV and the peripheral energy region 10-50 keV, and additionally 50-1000 keV.

Figure 5C:
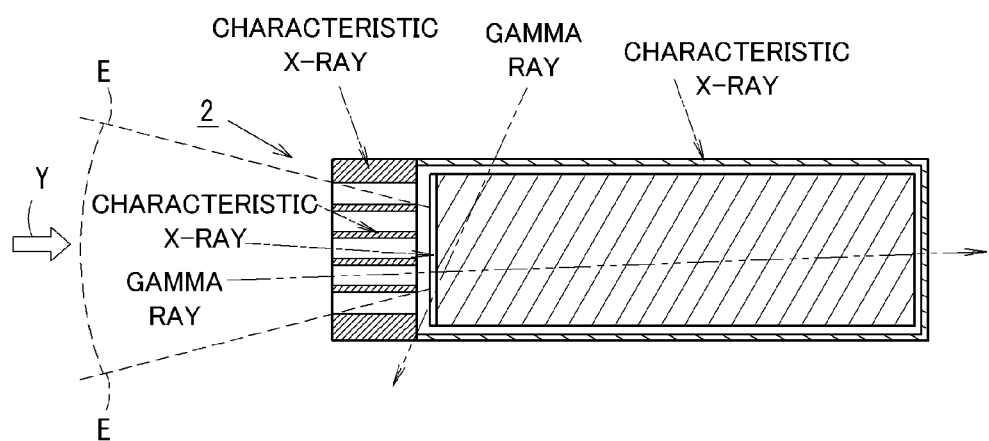

FIGS. 5A and 5C are explanatory views for explaining a constitution of the radioactive substance detection device 2. FIG. 5A is a perspective view showing a schematic constitution of the radioactive substance detection device 2, FIG. 5B is a longitudinal section view showing a schematic constitution of the radioactive substance detection device 2, and FIG. 5C is an explanatory longitudinal section view explaining passing/screening of characteristic X-rays and gamma rays for the radioactive substance detection device 2.

As shown in FIG. 5B, the radioactive substance detection device 2 has a screening container 25 having a cylindrical lateral wall 25b, an opening 25a on one side, and a bottom 25c on the other side. The screening container 25 is formed of SUS having a thickness of 1 mm.

To the opening 25a of the screening container 25, an approximately cylindrical collimator 21 (multiple collimator) is attached without any gap therebetween. The collimator 21 is formed of SUS, and has a plurality (19 in this example) of holes 22 that are arranged regularly. Thickness of the collimator 21 may be 1 mm, however, in the present embodiment, the thickness (thickness in the longitudinal direction of the cylinder) is 25 mm. The hole 22 has φ10 mm, and an interim part 23 (effective thickness) between neighboring holes 22 is 1 mm. The collimator 21 determines an angular resolution (full width at half maximum) of ±7.75°, and a maximum field of view of ±21.8°. The angular resolution and the maximum field of view determined by the collimator 21 can be set at arbitrary values by changing the diameter of the hole 22 and the thickness of the collimator 21 in the longitudinal direction (arriving direction of radiation). Also, the number of the holes 22 of the collimator 21 may be any value, and the number may be 1 (single collimator).

Thickness of the collimator 21 (effective thickness) is configured to be $1.6\lambda_5$ or more in a unit of mean free path ($\lambda_5$) of characteristic X-rays of a radioactive substance to be measured in the collimator 21.

Thickness of the interim part 23 between the holes 22 of the collimator 21, namely, the effective thickness of the collimator is configured to be $1.6\lambda_5$ or more in a unit of mean free path ($\lambda_5$) of characteristic X-rays radiated from a radioactive substance to be measured in the collimator 21, and to be $0.22\lambda_6$ or less in a unit of mean free path ($\lambda_6$) of gamma rays radiated at the highest proportion from a radioactive substance to be measured in the collimator 21.

These collimator 21 and screening container 25 function as a screening body.

Inside the screening container 25, a disc-like radiation detection element 26 is provided close to the back surface of the collimator 21, and also a photomultiplier 27 is provided. In other words, from the arriving direction of radiation, the collimator 21, the radiation detection element 26, and the photomultiplier 27 are arranged in sequence.

As the radiation detection element 26, a scintillator is used in the present embodiment, and concretely, it is formed of CsI into a shape of φ50 mm and 1 mm thick. The energy resolution of the radiation detection element 26 is 10.5 keV (full width at half maximum) at 32.2 keV.

For enabling measurement of characteristic X-rays (Ba—Kα: 32.2 keV, Cs—Kα: 31.0 keV, Xe—Kα: 29.8 keV, I—Kα: 28.6 keV, Te—Kα: 27.5 keV) radiated from either one or more than one of gamma ray radiating nuclides (hereinafter, radioactive substance) including barium, cesium, xenon, iodine, and tellurium as detection examples, the radiation detection element 26 measures spectra in the vicinity of peaks of these characteristic X-rays over at least part of the range from 20 keV to 40 keV. For accurate measurement, it can measure over the range from 10 keV to 50 keV. For identifying the kind of the radioactive substance more specifically, it can measure over the range of 50-1000 keV.

In the radiation detection element 26, the part where characteristic X-rays having passed through the hole 22 of the collimator 21 enter is a sensitive part 26a.

The photomultiplier 27 amplifies incident light inside and outputs it as an electric signal. When radiation enters the scintillator such as CsI which is the radiation detection element 26 and the scintillator emits light, the photomultiplier 27 converts the light to electrons and amplifies them to generate an electric signal.

The radioactive substance detection device 2 configured in this manner detects characteristic X-rays arriving from the specified direction Y as indicated by the arrow, as shown in FIG. 5C, and does not detect characteristic X-rays arriving from other directions and most of gamma rays from every direction. In other words, since the radiation detection element 26 is surrounded by the screening container and the collimator, the angle of incidence of characteristic X-rays is limited within the range of region E by the hole 22 of the collimator 21. By the incident characteristic X-rays, the radiation detection element 26 emits light, and the light is detected as an electric signal by the photomultiplier 27.

Characteristic X-rays arriving from other directions are screened out by the collimator 21 and the screening container 25, so that they will not cause light emission of the radiation detection element 26 and will not be detected.

Since most of gamma rays from every direction do not interact with the collimator 21 and the screening container 25, and also do not interact with the screening container 25 and the radiation detection element 26, they are not detected. Therefore, gamma rays are prevented from interrupting detection of characteristic X-rays.

In this manner, by the radiation detection element 26 and the photomultiplier 27, and the signal processing circuits (3, 4, 5) by the pre-amplifier 3, the waveform shaping amplifier 4, and the peak sensitive ADC 5, shown in FIG. 4, energy information of characteristic X-rays radiated from radioactive substances and incident intensity of characteristic X-rays are acquired.

Figure 6:
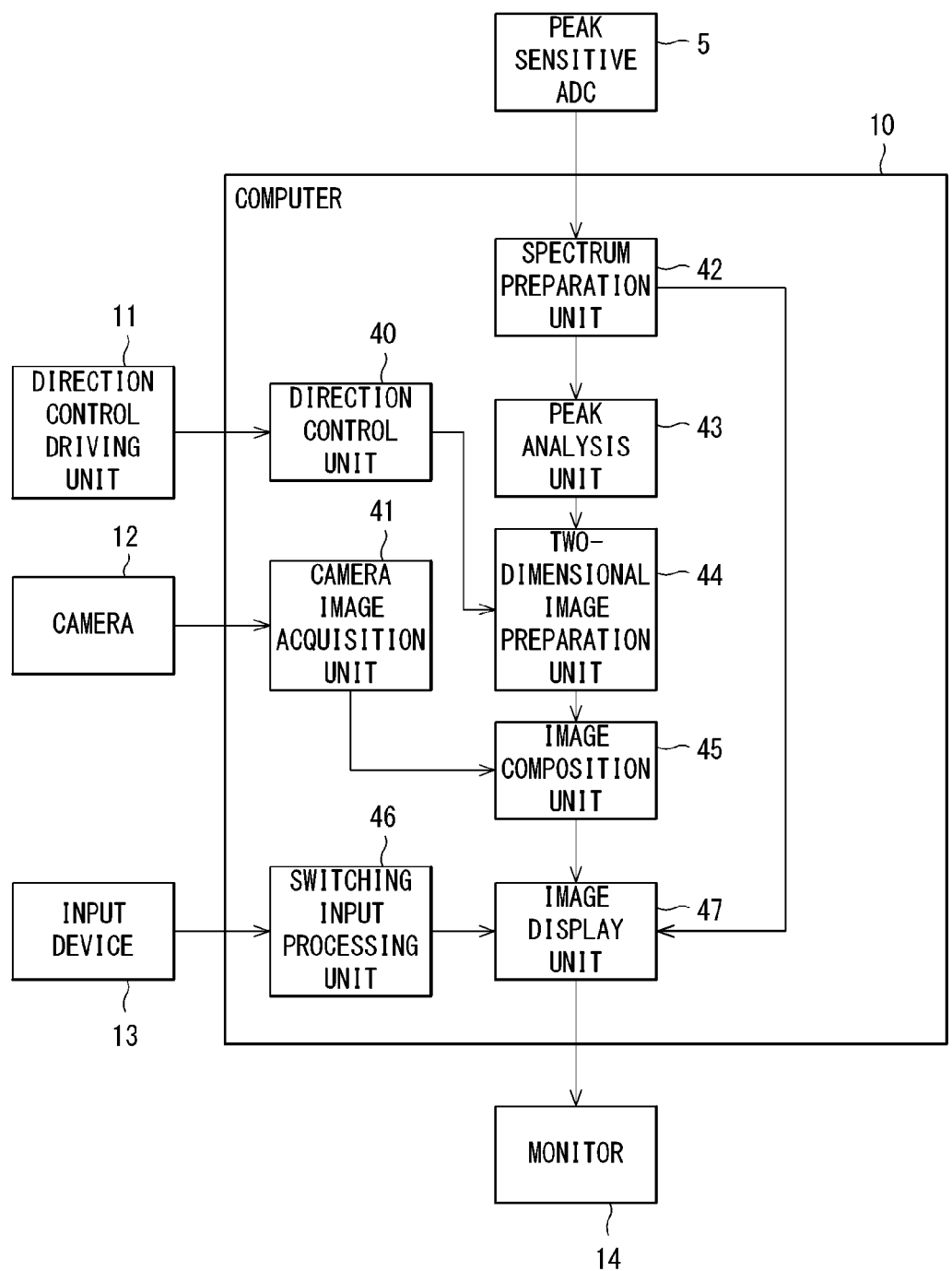
FIG. 6 is a functional block diagram showing the function of a computer.

FIG. 6 shows a functional block diagram when the control unit 10c operating according to the program in the storage unit 10b functions as respective functional means in the computer 10 (see FIG. 4).

As functional blocks of the computer 10, a direction control unit 40, a camera image acquisition unit 41, a spectrum preparation unit 42, a peak analysis unit 43, a two-dimensional image preparation unit 44, an image composition unit 45, a switching input processing unit 46, and an image display unit 47 are provided.

The direction control unit 40 controls driving of the direction driving control unit 11, and controls the direction of the camera 12 and the direction of the radioactive substance detection device 2 (see FIG. 4). Concretely, first, direction of the camera 12 is controlled and an imaging range is defined. Then the imaging range of the camera 12 is divided into a plurality of regions in a matrix (lattice) form, and the radioactive substance detection device 2 is directed to one of the regions. After completion of detection of the region, the radioactive substance detection device 2 is directed to the next region. By repeating this direction control, the direction control unit 40 is able to detect characteristic X-rays radiated from radioactive substances for every region divided into a matrix form.

The camera image acquisition unit 41 acquires a camera image photographed from the camera 12 (see FIG. 4). This camera image acquisition unit 41 is configured to acquire a still image from the camera 12, but the configuration is not limited to this. For example, the camera image acquisition unit 41 may be configured to have a video camera in place of the camera 12, and acquire a motion image (video image) imaged by the video camera.

The spectrum preparation unit 42 processes data received from the peak sensitive ADC 5 and prepares an energy spectrum.

The peak analysis unit 43 finds out a single peak of characteristic X-ray from the spectrum received from the spectrum preparation unit 42, and determines its net count. Alternatively, in the field where a plurality of radioactive substances coexist, the peak analysis unit 43 finds out a plurality of peaks formed by a plurality of characteristic X-rays when the energy resolution is excellent, and finds out a peak compositely formed by a plurality of characteristic X-rays when the energy resolution is not excellent, and calculates the net count.

The peak analysis unit 43 also functions as a radioactive substance discrimination unit that executes the above-described first method of radioactive substance identification in specified direction by a daughter nuclide identification process, and executes the above-described second method of radioactive substance identification in specified direction by a candidate identification process and a kind discrimination process. The peak analysis unit 43 that executes the daughter nuclide identification process identifies the kind of daughter nuclide by the low energy region radioactive substance identification method (first process of radioactive substance identification in specified direction). The peak analysis unit 43 that executes the candidate identification process identifies the kind of parent nuclide by the above-described high energy region radioactive substance identification method. The peak analysis unit 43 that executes the kind discrimination process estimates energy and intensity of characteristic X-ray by the above-described characteristic X-ray peak estimation method, and discriminates the kind of radioactive substance in the specified direction by the above-described low energy region radioactive substance detailed identification method (second process of radioactive substance identification in specified direction).

The two-dimensional image preparation unit 44 prepares an image showing direction to a radioactive substance based on the net count of characteristic X-ray peaks in the peak analysis unit 43. This image may be, for example, a matrix image. In other words, since presence of radioactive substance in each region is detected by the radioactive substance detection device 2, driving direction driving control unit 11 by the direction control unit 40, it is possible to prepare a matrix image that indicates quantity of radioactive substance for each region by filling each region at a density corresponding to the detection level.

The spectrum preparation unit 42 transmits a plurality of spectrum images obtained in respective regions divided into a matrix form (16 spectrum images in this embodiment) to the image display unit 47.

The image composition unit 45 prepares a composite image by composition of a photographed image acquired in the camera image acquisition unit 41, and a matrix-like two-dimensional image prepared in the two-dimensional image preparation unit 44. In this manner, the position on the matrix where a radioactive substance is detected and the position of the radioactive substance in the photographed image are brought into correspondence with each other.

The switching input processing unit 46 accepts an operation input for switching the image to be displayed on the monitor 14 between a spectrum image and an obtained image (operation input via the input device 13).

Figure 7:
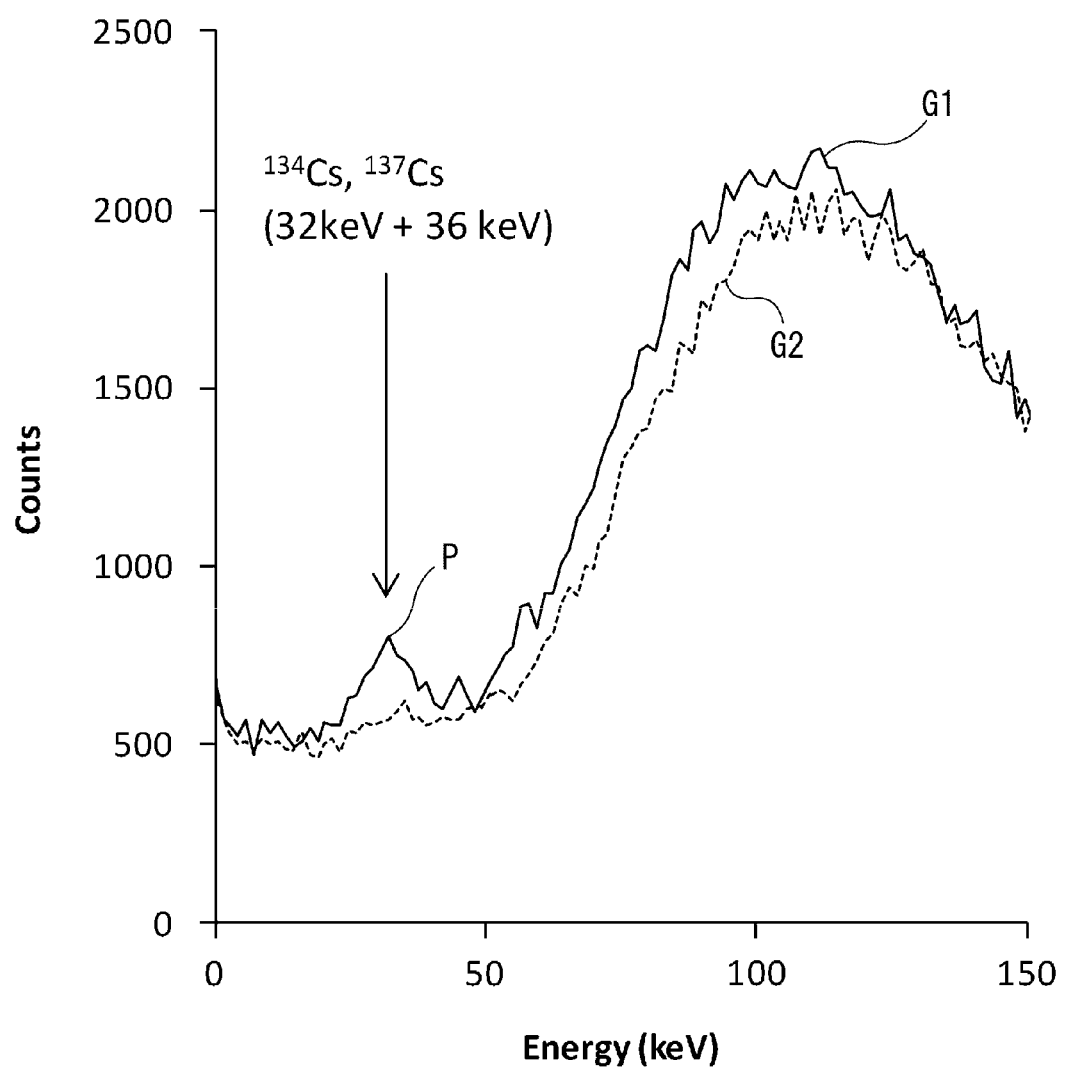
FIG. 7 is an explanatory chart by a graph showing a detection result by the radiation source location visualization system.
Figure 8:
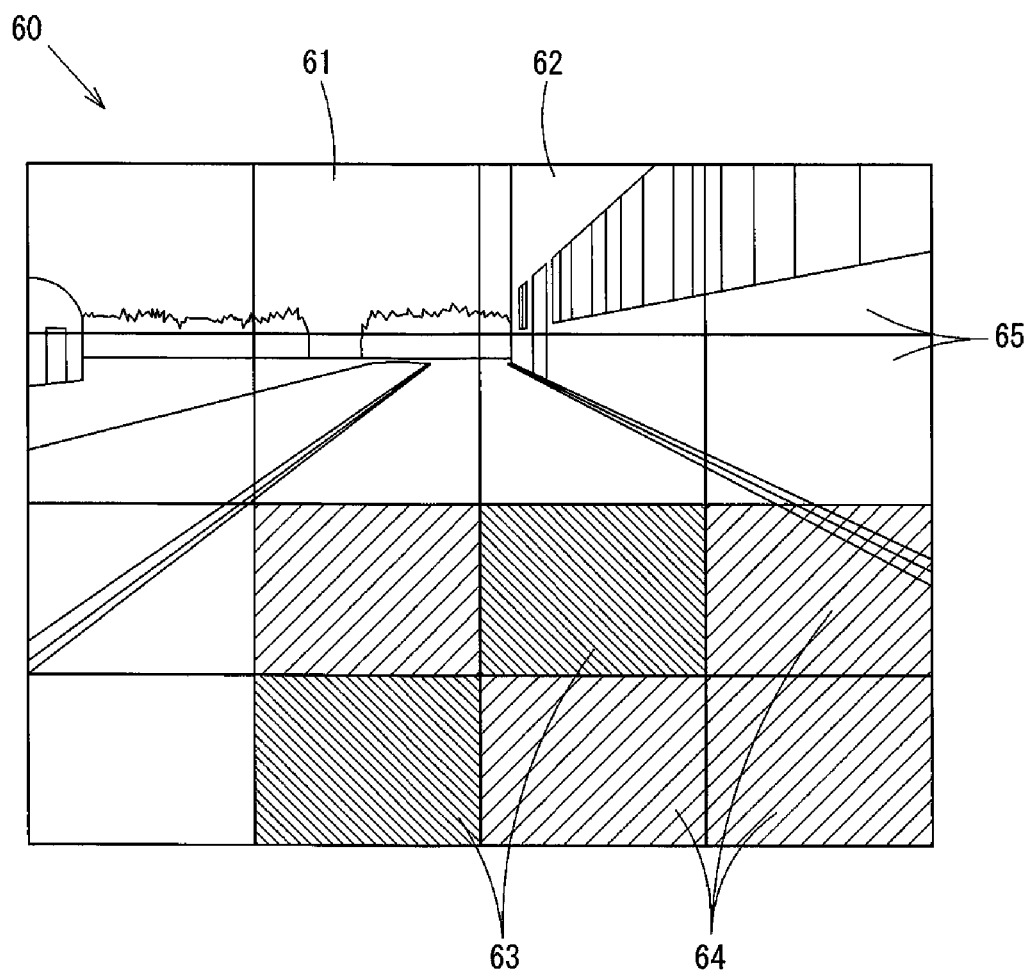
FIG. 8 is a screen configuration view of an imaging image by the radiation source location visualization system.

The image display unit 47 displays the spectrum image shown in FIG. 7 and the obtained image shown in FIG. 8 on the monitor 14. In response to an operation input by the switching input processing unit 46, if the spectrum image is designated and one of the regions divided into a matrix form is designated, the spectrum image as shown in FIG. 7 is displayed, and if the two-dimensional image is designated, the composite image as shown in FIG. 8 is displayed.

In this manner, it is possible to detect characteristic X-rays, to display the spectrum image of radioactive substances in the graph shown in FIG. 7, and to display the detection position in the composite image in a matrix form as shown in FIG. 8.

FIG. 7 is a graph showing a spectrum of detected radiation. The horizontal axis represents energy (keV) and the vertical axis represents the number of counts of radiation. Graph G1 shows an example of measurement directed to the direction in which a radioactive substance is present (contamination direction), and graph G2 shows an example of measurement directed to the direction in which a radioactive substance is not present (non-contamination direction).

The radiation source location visualization system 1 used for the measurement for this graph utilizes R10131 available from Hamamatsu Photonics K.K. as the photomultiplier 27 shown in FIG. 4, type 595H available from CLEAR-PULSE CO., LTD. as the pre-amplifier 3, type 4417 available from CLEAR-PULSE CO., LTD. as the waveform shaping amplifier 4, 8100A available from AMPTEK as the peak sensitive ADC 5, and C9619-01 available from Hamamatsu Photonics K.K. as the high-voltage power supply 9.

As shown in this graph, in the detection directed to the non-contamination direction, no radioactive substance is detected, however, in the detection directed to the contamination direction, peak P detecting 32 keV and 36 keV from $^{134}$Cs and $^{137}$Cs is observed. Accordingly, a characteristic X-ray of 32 keV and 36 keV from $^{134}$Cs and $^{137}$Cs can be detected. In this manner, the monitor 14 that displays a spectrum of radiation functions as a peak output unit that outputs a peak of characteristic X-ray.

This detection of peak P may be executed by the control unit 10c of the computer 10 (see FIG. 4). To be more specific, template data is preliminarily stored in the storage unit 10b of the computer 10 (see FIG. 4). Then the control unit 10c calculates a projecting amount of the measurement data (spectrum of detected radiation) from the template data, and detects the position (energy (keV)) where the projecting amount is largest as peak P. The template data may be such data that a graph shape without peak P as is graph G2 is approximated by a predetermined function (for example, quartic function) from the low energy region to the high energy region. A plurality of template data may be used, and in particular, in such an environment that a wide mountain-shaped peak (the one having a peak position between 60 keV and 250 keV, full width at half maximum between 60 keV and 200 keV, and not being a line gamma ray peak or a characteristic X-ray peak) appears more strongly than peak P on the high energy side of peak P, for example, because of abundance of ordinary substances around the radioactive substance (around radiation source), data of a predetermined function having a shape following the wide mountain-like peak part can be employed as the template data. The line gamma ray peak means a peak having energy corresponding to the excitation level difference of the nucleus of the radioactive substance (daughter nuclide).

As a result, the control unit 10c is able to detect peak P appropriately even when the wide mountain-shaped peak on the high energy side of peak P is stronger than peak P. Also, by determining an area (net count) of the part (peak P peripheral part) projecting from the template data in the measurement data, it is possible to calculate the amount of the radioactive substance being present in the specified direction which is the detection direction of the characteristic X-ray. The control unit 10c that outputs peak P detected in this manner also functions as a peak output unit.

In this detection of peak P, the control unit 10c also executes identification of the kind of radioactive substance. In this case, the control unit 10c identifies candidates for the kind of radioactive substance in the gamma ray region by the above-described candidate identification process, and discriminates the kind of radioactive substance being present in the specified direction among the candidates in the characteristic X-ray region by the kind discrimination process. The control unit 10c that executes identification of the kind of radioactive substance functions as a radioactive substance discrimination unit.

FIG. 8 is a screen explanatory view showing a composite image 60. In the composite image 60, on a photographed image 61 photographed by the camera 12, a two-dimensional image 62 of a matrix form where each cell is filled according to the characteristic X-ray intensity is superposed (translucent composition). The two-dimensional image 62 is divided into a plurality of cells (16 in the depicted example), and characteristic X-ray intensity is displayed for each cell. For example, a first intensity display part 63 having high characteristic X-ray intensity, a second intensity display part 64 having lower characteristic X-ray intensity, and a third intensity display part 65 where radiation is little detected are displayed. This makes it possible to check how much radioactive substance is present in what region. In this manner, the monitor 14 that displays characteristic X-ray intensity functions as a composite image output unit that outputs a composite image.

The color of filling display of each region differs depending on the kind of the discriminated radioactive substance. The kind of the radioactive substance indicated by each color is displayed on the screen. Alternatively, it is indicated by an appropriate method, for example, it is indicated in a manual, separately. The identified kind of radioactive substance may be clearly shown on the screen. The two-dimensional image 62 may be prepared for each discriminated kind of radioactive substance. In this case, the monitor 14 may perform display appropriately, for example, various kinds of two-dimensional images 62 may be switchable with a switching button, or a plurality of two-dimensional images 62 may be displayed side-by-side in a single screen.

With the above constitution, the radioactive substance detection device 2 is able to measure a radioactive substance radiating gamma rays and characteristic X-rays and to create an image of distribution of the radioactive substance with sufficient performance and with a very lightweight configuration. In other words, in contrast to the conventional case where thick lead and scintillator are used, the radioactive substance detection device 2 allows reduction in weight of the screening body to at least about one-eighteenth or less of the conventional one by the thin screening container 25 (for example, SUS of 1 mm thick) and the thin collimator 21, and the thin radiation detection element 26 (for example, CsI of 1 mm thick). Further, by optimization of the screening body (screening container 25 and collimator 21), the weight of the screening body can be reduced to one-fiftieth or less of the conventional one. For obtaining 98% of the screen factor of the screening body in detecting $^{137}$Cs, a conventional gamma camera requires lead of 34 mm, however, the radioactive substance detection device 2 realizes weight reduction of about one-fifties ([34 mm×specific gravity of lead 11.3]/[1 mm×specific gravity of SUS 7.9]) of the conventional one while the screening body has equivalent directive property with the conventional one because 98% of screen factor of the screening body can be realized by 1 mm of SUS. The radioactive substance detection device 2 is able to recognize at least presence of a radioactive substance, and to create an image of distribution of radioactive substance, and can achieve quantification of radioactive substance or identification of the kind of radioactive substance as is necessary.

Furthermore, the screening container 25 may have such a thickness that is useless for screening out gamma rays arriving from every direction, and is unusable in a conventional technique. The thickness 23 between the holes 22 of the collimator 21, namely the effective thickness of the collimator may be such a thickness that is useless for screening out gamma rays arriving from every direction, and is unusable in a conventional technique. In addition, the radiation detection element 26 may have such a thickness that is useless for detecting gamma rays, and is unusable in a conventional technique. With such a thickness, a radioactive substance that radiates gamma rays can be detected by utilizing characteristic X-ray.

The signal processing circuits (3, 4, 5) (see FIG. 4) detect a spectrum in the vicinity of a peak of characteristic X-ray (for example, 32 keV to 36 keV in the case of $^{137}$Cs). By selecting characteristic X-rays as a target to be measured in this manner, it is possible to thin the screening container 25, thin the radiation detection element 26, and reduce the weight of the collimator 21 as described above. Also, with such signal processing circuits (3, 4, 5), it is possible to provide the radioactive substance detection device 2 having excellent sensitivity.

The radiation detection element 26 is formed so that the thickness of the sensitive part with respect to the incidence direction of the characteristic X-ray is $1.1\lambda_1$ or more in a unit of mean free path ($\lambda_1$) of characteristic X-rays of the radioactive substance to be measured in the substance used for the radiation detection element 26, and the gamma rays radiated with the highest emission probability among all of the gamma rays with variety of energies from a radioactive substance to be measured is in the range of $0.14\lambda_2$ or less in a unit of mean free path ($\lambda_2$) in the substance used for the radiation detection element 26. As a result, it is possible to suppress the background and improve the sensitivity to characteristic X-rays.

The screening container 25 is formed to have a thickness that is $1.6\lambda_3$ or more in a unit of mean free path ($\lambda_3$) in the screening container 25 of characteristic X-rays of the radioactive substance to be measured, and $0.22\lambda_4$ or less in a unit of mean free path ($\lambda_4$) in the screening container 25 of gamma rays radiated with the highest emission probability among all of the gamma rays with variety of energies from a radioactive substance to be measured. As a result, it is possible to improve the sensitivity to characteristic X-rays while reducing the weight.

Thickness 23 between the holes 22 of the collimator 21, namely the effective thickness of the collimator is formed within the range of $1.6\lambda_5$ or more in a unit of mean free path ($\lambda_5$) in the substance of the collimator 21 of the characteristic X-rays of the radioactive substance to be measured and $0.22\lambda_6$ or less in a unit of mean free path ($\lambda_6$) in the substance of the collimator 21 of the gamma ray radiated with the highest emission probability among all of the gamma rays with variety of energies from a radioactive substance to be measured. As a result, it is possible to improve the sensitivity to characteristic X-rays while reducing the weight.

The signal processing circuits (3, 4, 5) can measure from 10 keV to 50 keV. As a result, it is possible to accurately measure nuclides (radioactive substances) of barium, cesium, xenon, iodine, and tellurium that radiate gamma rays and characteristic X-rays simultaneously by utilizing characteristic X-rays.

Also, the radiation source location visualization system 1 is able to display the position where a nuclide of radioactive substance is present in the composite image 60 (see FIG. 8). As a result, it is possible to check the position of the radiation source on the image, and to easily identify the contamination position. Further, the radiation source location visualization system 1 is able to display the spectrum of the detected radiation as graph G1 (see FIG. 7).

Since the radiation detection element 26 only has to stop and detect characteristic X-rays, even with a material such as CdTe having technical difficulty in operating the radiation detection element at high performance while keeping large area by having large thickness (for example, up to about 5 mm thick for CdTe), it can be utilized with optimum thickness (for example, 1 mm thick).

Also, it is possible to achieve detection efficiency of about 80% or more (95% for 32 keV of $^{137}$Cs in the case of 1 mm of CsI) for characteristic X-rays by the radioactive substance detection device 2, and to detect $^{137}$Cs at a comparable count efficiency to a conventional gamma camera, with very lightweight compared with the conventional one.

To be more specific, radiation probabilities of gamma rays of 662 keV and characteristic X-rays of 32 keV per one decay of $^{137}$Cs are 85.1% and 5.6%, respectively. Many conventional gamma cameras that are already brought into practical use aim at detecting gamma rays of 662 keV whose radiation probability is as high as 85.1%, and the detection efficiency for 662 keV of $^{137}$Cs is about 5% to 10%. This conventional gamma camera will achieve a detection efficiency of about 30% if a fluorescent screen of large size (for example, NaI of 50 mm diameter×30 mm thick) is used, however, such a configuration will interfere with use because the weight of the screening body surrounding the fluorescent screen further increases.

In contrast to this, the radioactive substance detection device 2 of the present invention can achieve detection efficiency of as high as about 80% or more although it is intended to detect characteristic X-rays whose radiation provability per one decay of $^{137}$Cs is 5.6%, which is smaller than that of gamma rays. As a result, the radioactive substance detection device 2 can detect $^{137}$Cs at a comparable count efficiency to a conventional gamma camera, with a configuration that is much lighter than the conventional gamma camera. Further, since the radioactive substance detection device 2 is much lighter than a conventional gamma camera, it is possible to easily double, quintuple, decuple, or further increase the sensitive area of the radioactive substance detection element or the number of the radioactive substance detection device without worrying about the weight, and to increase the sensitivity.

Further, the radioactive substance detection device 2 is able to suppress the background and lower the detection limit by employing a specific thickness of the radiation detection element 26 even in an environment where gamma rays arrive from various directions, and to measure characteristic X-rays (in particular, those having energy amount of 20 keV to 40 keV) with high sensitivity that are conventionally difficult to be measured.

By enabling the signal processing circuit to measure spectrum from 10 keV, it is possible to increase the estimation accuracy of background in the vicinity of characteristic X-ray peak, and to determine the net count of characteristic X-rays accurately.

Also, by selecting the thickness of the screening container 25 and the thickness 23 between the holes 22 of the collimator 21 at specific thicknesses, the radioactive substance detection device 2 realizes significant weight reduction compared with a conventional gamma camera while realizing sufficient sensitivity for the direction in which a radioactive substance is present.

Further, by embodying the radiation detection element 26 by CsI of 1 mm thick, the following general performance for radiation can be obtained.
<X-Ray (32 keV)>
Probability of interaction is high (95% of the entirety stops completely).
<Gamma Ray (662 keV)>
Probability of interaction is low (97% of the entirety passes through without interacting).
By embodying the screening container 25 by SUS of 1 mm thick, the following general performance for radiation can be obtained.
<X-Ray ($^{137}$Cs-32 keV)>
Probability of interaction is high (98% of the entirety stops completely).
<Gamma Ray ($^{137}$Cs-662 keV)>
Probability of interaction is low (94% of the entirety passes through without interacting).

Further, it is possible to usually direct the radioactive substance detection device 2 and the camera 12 in the same direction by the direction control driving unit 11 and the direction control unit 40. By sequentially changing the direction of the camera 12 together with the radioactive substance detection device 2 by control driving or manually so that the imaging ranges neighbor, and arranging composite images of photographed image and two-dimensional image in each direction side by side and combining them in the image composition unit 45, it is also possible to obtain a panoramic composite image that is wider than the imaging range and the detection range.

While the direction control driving unit 11 and the direction control unit 40 are configured to be driven under control of the computer 10, they may be configured to be driven manually. In this case, such a configuration may be applicable that the direction control driving unit 11 and the direction control unit 40 are not provided, and measurement direction is inputted to the input device 13 while determining the direction by means of a mechanical direction fixing tool not using an electric signal. Also in this case, it is possible to prepare and display a composite image by using the radiation source location visualization system 1 configured by a single element module.

Second Embodiment

Figure 9A:
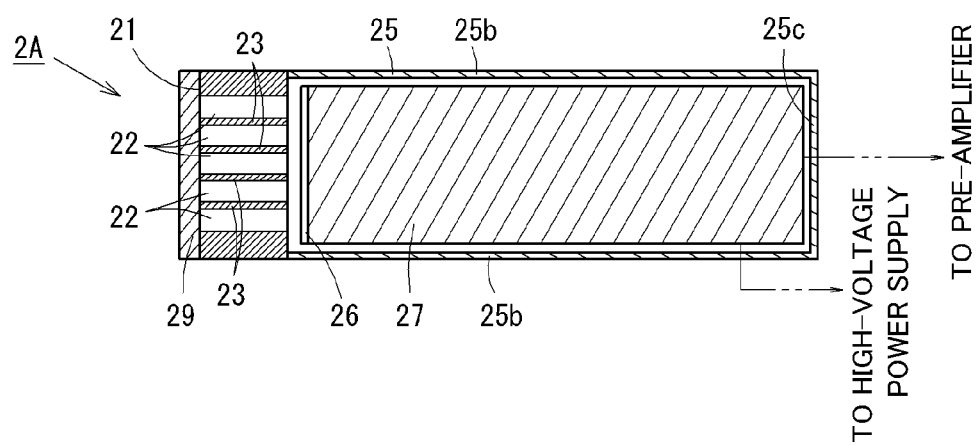
FIGS. 9A and 9B are explanatory views showing a longitudinal section of a radioactive substance detection device in second and third embodiments.

FIG. 9A is a longitudinal section view of a radioactive substance detection device 2A in a second embodiment. The radioactive substance detection device 2A is provided with a filter 29 on the front face side (on the side opposite to the photomultiplier 27 with respect to the radiation detection element 26) of the collimator 21. The filter 29 may be a filter that suppresses noises for improving the sensitivity to characteristic X-rays, and may be, for example, an acrylic plate that screens out β-rays. Concretely, a disc-like acrylic plate having, for example, a thickness of 6 mm, an area as same as that of the radiation detection element 26, and a diameter of 50 mm can be used.

Since other constituents of the radioactive substance detection device 2A are as same as those of the first embodiment, the same constituent is denoted by the same reference numeral, and detailed description thereof will be omitted.

By using the filter 29 as described above, it is possible to remove noises and to improve the sensitivity to characteristic X-rays. In particular, when an acrylic plate is used, β-rays that are likely to become noises can be screened out, and the sensitivity to characteristic X-rays can be further improved.

The filter 29 is not limited to one, but plural kinds of filters may be provided.

As the filter 29, one that screens out characteristic X-rays and β-rays may be used. In this case, for example, a disc-like SUS plate having a thickness of 1 mm, a diameter of 50 mm and an area as same as that of the radiation detection element 26 can be used. In the case of using the filter 29 that also screens out characteristic X-rays as described above, by taking a difference between a measurement result in the state where the filter 29 is attached and a measurement result in the state where the filter 29 is detached, it is possible to remove noises and to pick up a peak of characteristic X-ray. In other words, since in the measurement result in the state where the filter 29 is attached, noises by gamma rays can mainly be measured, it is possible to pick up only characteristic X-rays by taking a difference from the measurement result in the state where the filter 29 is detached.

Third Embodiment

Figure 9B:
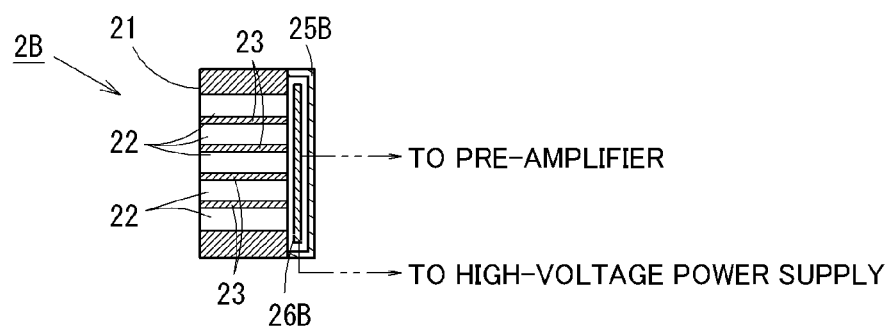

FIG. 9B is a longitudinal section view showing a radioactive substance detection device 2B using a semiconductor in place of the scintillator as the radiation detection element 26. As shown in the drawing, a radiation detection element 26B is covered with a screening container 25B, and the collimator 21 is attached to the front face (opening) of the screening container 25B.

The radiation detection element 26B is formed of a semiconductor such as CdTe.

The radiation detection element 26B is connected to the high-voltage power supply 9 (see FIG. 4) and the pre-amplifier 3 (see FIG. 4), and its direction is controlled by the direction control device 11.

Since other constituents are as same as those of the first embodiment, the same constituent is denoted by the same reference numeral, and detailed description thereof will be omitted.

Even with such a configuration, the same operation and effect as those in the first embodiment can be obtained.

Unlike the first embodiment, since a device for reading out a fluorescent screen such as a photomultiplier is no longer required in a third embodiment, the screening body can be made more compact.

Fourth Embodiment

Figure 10:
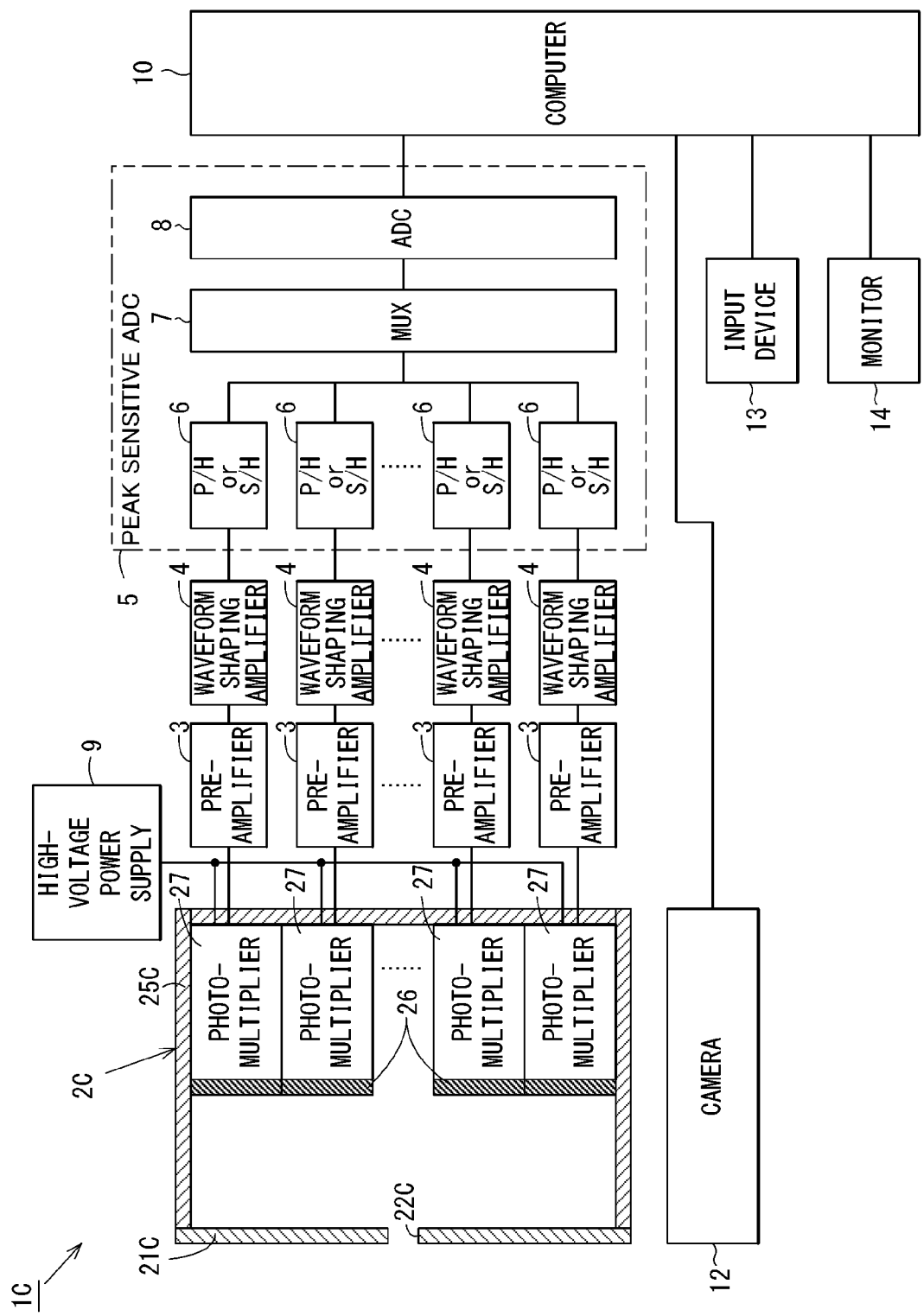
FIG. 10 is a block diagram of a radiation source location visualization system in a fourth embodiment.

FIG. 10 is a block diagram showing a system configuration of a radiation source location visualization system 1C in a fourth embodiment. The radiation source location visualization system 1C shows an example of a multi-element module.

In the radioactive substance detection device 2C, pairs of radiation detection elements 26 and photomultipliers 27 are arranged in plural in one screening container 25C in such a manner that detection planes of the radiation detection elements 26 are aligned on the same plane.

A collimator 21C (front plate) is a pinhole collimator composed of a thin material having such a thickness that allows gamma rays to sufficiently pass through while sufficiently screening out characteristic X-rays, and is provided with a hole 22C at one point in the vicinity of the center.

Thickness (effective thickness) of the collimator 21C is formed in the range of $1.6\lambda_5$ or more in a unit of mean free path ($\lambda_5$) of characteristic X-rays of the radioactive substance to be measured in the substance of the collimator 21C, and $0.22\lambda_6$ or less in a unit of mean free path ($\lambda_6$) of gamma rays radiated at the highest proportion from the radioactive substance to be measured in the substance of the collimator 21C. As a result, it is possible to improve the sensitivity to characteristic X-rays while reducing the weight.

To each of the plurality of photomultipliers 27, the high-voltage power supply 9, the pre-amplifier 3, and the waveform shaping amplifier 4 are connected. In the rear stage of the waveform shaping amplifier 4, the peak-hold circuit or sample-and-hold circuit 6, and the multiplexer 7 are provided, and signals from every waveform shaping amplifiers 4 are switched and processed. Also, each peak-hold circuit or sample-and-hold circuit 6 may be provided with an individual ADC (corresponding to ADC 8) without provision of the multiplexer 7, and a method of transmitting output from each ADC to the computer 10 may be employed.

Unlike the first embodiment, the radioactive substance detection device 2C does not have the direction control driving unit 11 (see FIG. 4) and the direction control unit 40 (see FIG. 6). In addition, the imaging range of the camera 12 and the detection range by the radioactive substance detection device 2C are coincident, and the detection range of the radioactive substance detection device 2C is divided into a matrix form, and one detection range of the radiation detection element 26 and the photomultiplier 27 corresponds to one cell of the matrix. The image composition unit 45 (see FIG. 6) prepares a composite image by superposing each cell of two-dimensional image on one photographed image.

Since other constituents are as same as those of the first embodiment, the same constituent is denoted by the same reference numeral, and detailed description thereof will be omitted.

Even with such a configuration, the same operation and effect as those in the first embodiment can be obtained.

By employing a multi-element module, it is possible to detect through a piece of processing which direction the characteristic X-rays from the radioactive substance come from. In other words, by discriminating the one of the radiation detection elements that has responded to a characteristic X-ray, it can be identified that the radiation comes from the direction of the straight line connecting the front face of the responded radiation detection element 26 to the hole 22C and from the range defined by the sizes of the radiation detection element 26 and the hole 22C.

Similarly to the first embodiment, the direction control driving unit 11 and the direction control unit 40 may be provided. In this case, it is also possible to obtain a panoramic composite image that is wider than the imaging range and the detection range.

Also, in the radioactive substance detection device 2C, the collimator 21C may be a coded mask type collimator (front plate) formed with a plurality of holes 22C in a desired arrangement. The arrangement of holes of the coded mask type collimator and so on in this case may be an arrangement and so on as described in the document "New family of binary arrays for coded aperture imaging" (APPLIED OPTICS, Vol. 28, No. 20, 15 Oct. 1989, 4344-4352, Stephen R. Gottesman and E. E. Fenimore).

Fifth Embodiment

Figure 11:
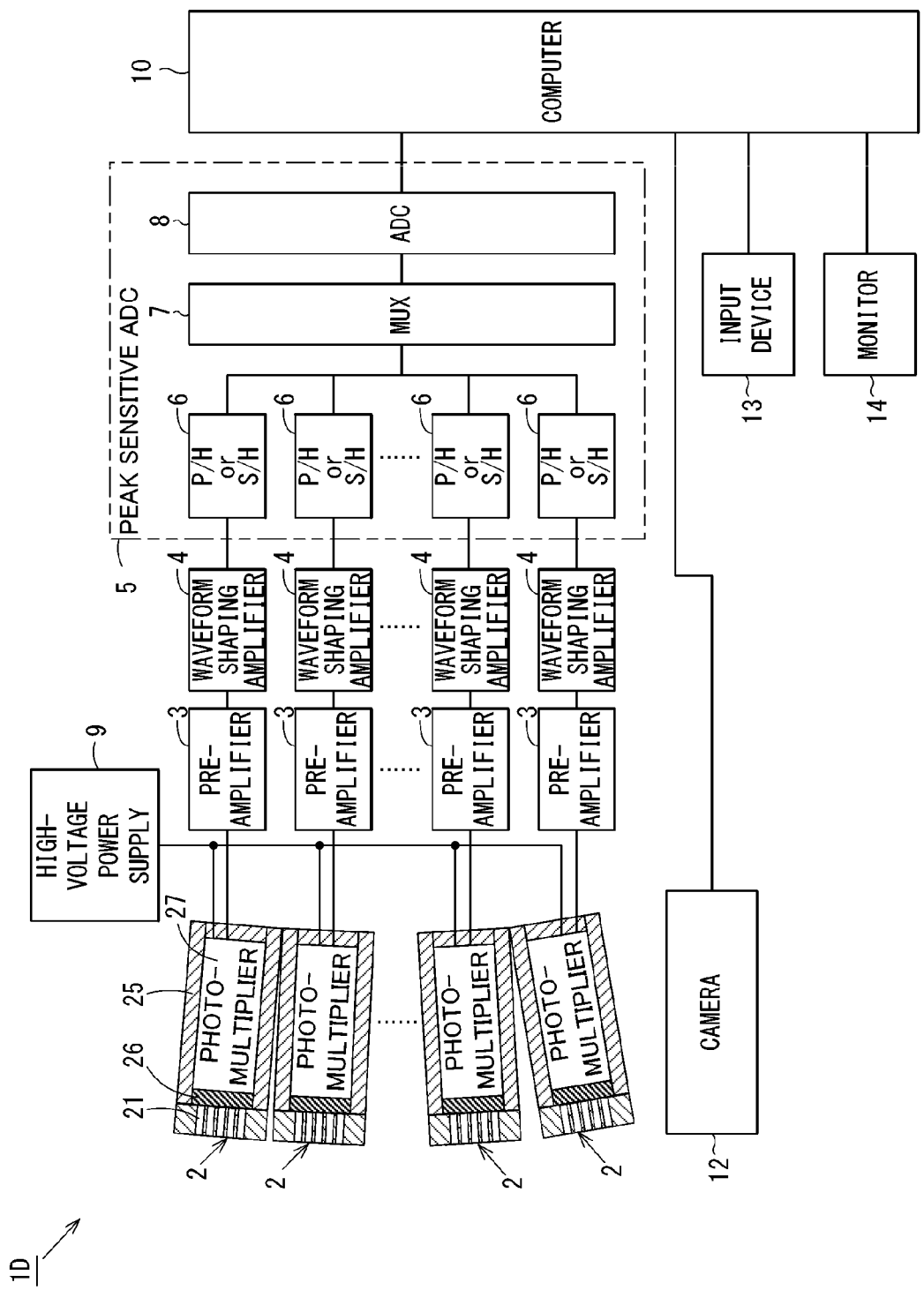
FIG. 11 is a block diagram of a radiation source location visualization system in a fifth embodiment.

FIG. 11 is a block diagram showing a system configuration of a radiation source location visualization system 1D in a fifth embodiment. The radiation source location visualization system 1D shows an example of a multi-element module.

The radiation source location visualization system 1D has a plurality of radioactive substance detection devices 2, which are fixed in such a manner that they are directed in different directions. In the rear stage of each radioactive substance detection device 2, one pre-amplifier 3, waveform shaping amplifier 4, and peak-hold circuit or sample-and-hold circuit 6 are provided. In the rear stage of the peak-hold circuit or sample-and-hold circuit 6, the multiplexer 7 is provided, and signals from every waveform shaping amplifier 4 are processed by signal switching. Also, each peak-hold circuit or sample-and-hold circuit 6 may be provided with an individual ADC (corresponding to ADC 8) without provision of the multiplexer 7, and a method of transmitting output from each ADC to the computer 10 may be employed.

Since other constituents are as same as those of the first embodiment, the same constituent is denoted by the same reference numeral, and detailed description thereof will be omitted.

Even with such a configuration, the same operation and effect as those in the first embodiment can be obtained. Further, by employing a multi-element module as described above, it is possible through a piece of processing to detect from which direction the characteristic X-ray emitted from the radioactive substance comes. In other words, by knowing from which radioactive substance detection device 2 the detection is made, it can be determined that radiation is detected from the front of the radioactive substance detection device 2 by which the detection is made.

Such a configuration is also possible that the plurality of radioactive substance detection devices 2 are provided, and part of the radioactive substance detection devices 2 are provided with the filter 29 (see FIG. 9A) for screening characteristic X-rays and β-rays described in the second embodiment.

In this case, it is possible to accurately detect characteristic X-rays in a short time by detecting noise components by gamma rays in the radioactive substance detection device 2 to which the filter 29 is attached, and detecting characteristic X-rays and noise component by gamma rays in the radioactive substance detection device 2 to which the filter 29 is not attached, and by taking a difference. In other words, it is possible to complete the detection by conducting both measurements with and without the filter 29 at once without necessity of conducting the measurements while attaching the filter 29 and then detaching the same.

The present invention is not limited to the configuration of the above-described embodiments, and many embodiments can be obtained.

For example, while a scintillator or a semiconductor is used as the radiation detection element 26, a semiconductor cooled by a cooling device or the like may also be used.

As the material of the screening container, not only SUS but appropriate substances that screen out characteristic X-rays such as materials containing brass or lead may be used.

The radioactive substance detection devices 2, 2A, 2B, 2C and the radiation source location visualization systems 1, 1C, 1D may also be used as a contamination detection device for detecting contamination by a radioactive substance.

By using the screening containers 25, 25B, 25C without using a collimator, each of the radioactive substance detection devices 2, 2A, 2B, 2C may be configured to determine a specified direction to be measured. Also in this case, it is possible to detect a radioactive substance in the specified direction that is not screened out by the screening containers 25, 25B, 25C, and to discriminate the kind of the radioactive substance.

INDUSTRIAL APPLICABILITY

The present invention is applicable to the use of determining the direction in which a radioactive substance radiating gamma rays and characteristic X-rays is present, and the quantity of the radioactive substance, and to other various uses of detecting a radioactive substance.

The invention claimed is:

1. A radioactive substance detection device that detects a radioactive substance being present in a specified direction, the radioactive substance detection device comprising:
 a radiation detection element having a thickness and an incident surface perpendicular to the thickness,
  wherein the radiation detection element stops and detects characteristic X-rays arriving at the incident surface from the radioactive substance that radiates both gamma rays and the characteristic X-rays, and
  the radiation detection element allows the gamma rays arriving at the incident surface from the radioactive substance to pass through the radiation detection element; and a screening body having a thickness, wherein the screening body covers at least a portion of the radiation detection element so that the screening body screens out characteristic X-rays of radiation which arrive from directions other than the specified direction,
wherein the screening body allows gamma rays of radiation which arrive from directions other than the specified direction to pass through the screening body.

2. The radioactive substance detection device according to claim 1, further comprising:
a peak output unit that outputs a peak of the characteristic X-ray detected by the radiation detection element.

3. The radioactive substance detection device according to claim 2, wherein the radiation detection element detects the characteristic X-ray having an energy peak in a range of 20 keV to 40 keV.

4. The radioactive substance detection device according to claim 1, wherein the radiation detection element is formed to have a thickness of a sensitive part with respect to an incident direction of a characteristic X-ray in the range of $1.1\lambda_1$ or more in a unit of mean free path ($\lambda_1$) of the characteristic X-ray of the radioactive substance to be measured in a substance used as the radiation detection element, and $0.14\lambda_2$ or less in a unit of mean free path ($\lambda_2$) of a gamma ray radiated at the highest probability from the radioactive substance to be measured in the substance used as the radiation detection element.

5. The radioactive substance detection device according to claim 1, wherein the screening body is formed to have a thickness in the range of $1.6\lambda_3$ or more in a unit of mean free path ($\lambda_3$) of a characteristic X-ray of the radioactive substance to be measured in a screening body substance, and $0.22\lambda_4$ or less in a unit of mean free path ($\lambda_4$) of a gamma ray radiated at the highest probability from the radioactive substance to be measured in the screening body.

6. The radioactive substance detection device according to claim 5, wherein the screening body includes either one or both of a screening container that screens out the periphery of the radiation detection element, and a collimator disposed on the side of a detection object of the radiation detection element, and the thickness of the screening body means:
thickness of an interim part between holes when the screening body is a multiple collimator formed of a plurality of holes;
thickness of a lateral wall of a hole when the screening body is a single collimator having only one hole;
thickness of a front plate provided with a hole when the screening body is a pinhole collimator which have one hole and is provided with a plurality of radiation detection elements behind;
thickness of a front plate provided with a hole when the screening body is a coded mask type collimator which have a plurality of holes and is provided with a plurality of radiation detection elements behind; and
thickness of a lateral wall positioned at least laterally of the radiation detection element when the screening body is the screening container.

7. The radioactive substance detection device according to claim 1, further comprising:
a storage unit that stores a template for use in analysis of a peak of the characteristic X-ray; and
an analysis unit that analyzes the peak of the characteristic X-ray by using the template and a spectrum detected by the radiation detection element,
wherein the template is data having a peak part that is positioned at 60-250 keV on a higher energy side than energy of the characteristic X-ray region, and is stronger than the peak of the characteristic X-ray.

8. The radioactive substance detection device according to claim 1, further comprising:
a radioactive substance discrimination unit that executes a candidate identification process for identifying a candidate of the kind of the radioactive substance by using a spectrum of a gamma ray region of the spectrum detected by the radiation detection element, and executes a kind discrimination process for discriminating the kind of the radioactive substance in the specified direction by discriminating, by using a spectrum of a characteristic X-ray region of the spectra detected by the radiation detection element, whether the radioactive substance identified by the candidate identification process is present in the spectrum.

9. A radiation source location visualization system comprising:
a plurality of the radioactive substance detection devices according to claim 1;
a camera that images the specified direction and acquires a photographed image;
a two-dimensional imaging unit that prepares a two-dimensional image for each detection region on the basis of the amounts of radioactive substance detected by each of the plurality of radioactive substance detection devices;
a composition unit that prepares a composite image by registering and combining the photographed image and the two-dimensional image; and
a display unit that displays the composite image.

10. A radioactive substance detection method using the radioactive substance detection device according to claim 1, the method comprising the steps of:
measuring a spectrum in the vicinity of a peak of a characteristic X-ray; and
recognizing at least presence of the radioactive substance based on the spectrum.

11. A directional radioactive substance detection device that detects a radioactive substance that radiates X-rays and gamma rays, comprising:
a screening container having a body shaped to form a cavity with an opening to the cavity, wherein the body of the screening container prevents 80% or more of the X-rays having a peak energy in a range of 20 keV to 40 keV from penetrating therethrough, and the opening allows the X-rays having the peak energy in the range of 20 keV to 40 keV to reach the cavity, and the screening container allows 80% or more of the gamma rays to pass therethrough; and
a radiation detection element having an incident surface arranged inside the cavity so that the incident surface faces the opening, wherein the radiation detection element stops and detects the X-rays having the peak energy in the range of 20 keV to 40 keV arriving at the incident surface through the opening, and the radiation detection element allows 80% or more of the gamma rays to pass therethrough.

12. The directional radioactive substance detection device according to claim 11, further comprising a collimator comprising a hole, the collimator being arranged at the opening so that the hole is aligned with the opening which allows the X-rays to enter the cavity via both the hole and the opening.

13. The directional radioactive substance detection device according to claim 12, wherein an angular resolution and a maximum field of view are determined by a diameter of the hole and a thickness of the collimator.

* * * * *